US012577230B2

(12) United States Patent
Bosser Artal et al.

(10) Patent No.: US 12,577,230 B2
(45) Date of Patent: Mar. 17, 2026

(54) 2-(3-PYRIDIN-2-YL-4-QUINOLIN-4-YL-PYRAZOL-1-YL)- ACETAMIDE DERIVATIVES AS INHIBITORS OF TRANSFORMING GROWTH FACTOR-BETA RECEPTOR I/ALK5

(71) Applicant: AGOMAB SPAIN S.L.U., Touro (ES)

(72) Inventors: Ramón Bosser Artal, Barcelona (ES); Begoña Pampín Casal, O Pino (ES); Julio Castro Palomino Laria, Mataró (ES)

(73) Assignee: AGOMAB SPAIN S.L.U., Touro (ES)

( * ) Notice: Subject to any disclaimer, the term of this patent is extended or adjusted under 35 U.S.C. 154(b) by 407 days.

(21) Appl. No.: 18/246,903

(22) PCT Filed: Sep. 29, 2021

(86) PCT No.: PCT/EP2021/076730
§ 371 (c)(1),
(2) Date: Mar. 28, 2023

(87) PCT Pub. No.: WO2022/069509
PCT Pub. Date: Apr. 7, 2022

(65) Prior Publication Data

US 2023/0373966 A1 Nov. 23, 2023

(30) Foreign Application Priority Data

Sep. 30, 2020 (EP) .................................... 20382861

(51) Int. Cl.
*C07D 401/14* (2006.01)
*C07D 453/02* (2006.01)

(52) U.S. Cl.
CPC ......... *C07D 401/14* (2013.01); *C07D 453/02* (2013.01)

(58) Field of Classification Search
CPC .................................................. C07D 401/14
USPC ........................................................ 514/210
See application file for complete search history.

(56) References Cited

U.S. PATENT DOCUMENTS

| | | | |
|---|---|---|---|
| 6,525,059 | B1 | 2/2003 | Anantanarayan et al. |
| 11,040,976 | B2 | 6/2021 | Maianti et al. |
| 2021/0002265 | A1 | 1/2021 | Katanaev et al. |
| 2021/0261532 | A1 | 8/2021 | Lennek et al. |
| 2022/0411426 | A1 | 12/2022 | Maianti et al. |

FOREIGN PATENT DOCUMENTS

| | | | |
|---|---|---|---|
| CN | 110433164 | A | 11/2019 |
| WO | 02066462 | A1 | 8/2002 |
| WO | 2004026302 | A1 | 4/2004 |
| WO | 2004026306 | A2 | 4/2004 |
| WO | 2004072033 | A2 | 8/2004 |
| WO | 2011076725 | A1 | 6/2011 |
| WO | 2012051361 | A1 | 4/2012 |
| WO | 2016172631 | A3 | 12/2016 |
| WO | 2019166616 | A1 | 9/2019 |
| WO | 2020033413 | A3 | 5/2020 |
| WO | 2021105317 | A1 | 6/2021 |

OTHER PUBLICATIONS

Li et al., Synthesis and evaluation of the HIF-1α inhibitory activity of 3(5)-substituted-4-(quinolin-4-yl)- and 4-(2-phenylpyridin-4-yl) pyrazoles as inhibitors of ALK5, Bioorganic & Medicinal Chemistry Letters, Nov. 2019, vol. 30 (126822), pp. 1-12 (Year: 2019).*

Tojo M. et al., "The ALK-5 inhibitor A-83-01 inhibits SMAD signaling and epithelial-to-mesenchymal transition by transforming growth factor-B" Cancer Science, Oct. 17, 2005, vol. 96, No. 11, p. 791-800.

Akhurst R J et al., "Targeting the TGFβ signalling pathway in disease", Nature/Reviews, Oct. 2012, vol. 11(10):790-811.

Dewang, Purushottam M, and Dae-Kee Kim. "Synthesis and Biological Evaluation of 2-Pyridyl-Substituted Pyrazoles and Imidazoles as Transforming Growth Factor-b Type 1 Receptor Kinase Inhibitors." Bioorganic Medicinal Chemistry Letters, vol. 20, No. 14, 2010, pp. 4228-4232.

Gellibert, Francoise, et al. "Identification of 1,5-Naphthyridine Derivatives as a Novel Series of Potent and Selective TGF-β Type I Receptor Inhibitors." Journal of Medicinal Chemistry, vol. 47, No. 18, 2004, pp. 4494-4506.

Jin, Cheng Hua, et al. "Discovery of N-((4-([1,2,4]Triazolo[1,5-a]Pyridin-6-Yl)-5-(6-Methylpyridin-2-Yl)-1H-Imidazol-2-Yl)Methyl)-2-Fluoroaniline (EW-7197): A Highly Potent, Selective, and Orally Bioavailable Inhibitor of TGF-Beta Type I Receptor Kinase as Cancer Immunotherapeutic/Antifibrotic Agent." Journal of Medicinal Chemistry, vol. 57, No. 10, 2014, pp. 4213-4238.

Jin, Cheng Hua, et al. "Synthesis and Biological Evaluation of 1-Substituted-3(5)-(6-Methylpyridin-2-Yl)-4-(Quinoxalin-6-Yl)Pyrazoles as Transforming Growth Factor-β Type 1 Receptor Kinase Inhibitors." European Journal of Medicinal Chemistry, vol. 46, No. 9, 2011, pp. 3917-3925.

(Continued)

*Primary Examiner* — Jeffrey H Murray
*Assistant Examiner* — Rilla Marie Samsell
(74) *Attorney, Agent, or Firm* — ArentFox Schiff LLP

(57) ABSTRACT

The present invention relates to novel 2-(3-pyridin-2-yl-4-quinolin-4-yl-pyrazol-1-yl)-acetamide derivatives as potent inhibitors of transforming growth factor-β receptor I, (also named activin receptor-like kinase 5) (TGFβRI)/ALK5. Other objectives of the present invention are to provide a procedure for preparing these compounds; pharmaceutical compositions comprising an effective amount of these compounds; the use of the compounds for manufacturing a medicament for the treatment of pathological conditions or diseases that can improve by inhibition of transforming growth factor-β receptor I (TGFβRI)/ALK5, such as respiratory diseases including idiopathic pulmonary fibrosis, asthma, COPD and lung cancer, and dermal and ocular fibrotic conditions.

30 Claims, No Drawings

(56) References Cited

OTHER PUBLICATIONS

Li, Yan-Wei, et al., "Synthesis and evaluation of the HIF-1a inhibitory activity of 3(5)-substituted-4-(quinolin-4-yl)-and 4-(2-phenylpyridin-4-yl)pyrazoles as inhibitors of ALK5." Bioorganic Medicinal Chemistry Letters, Amsterdam, NL (2020) vol. 30, No. 2, Nov. 17, 2019, pp. 1-12.
PCT International Search Report and Written Opinion, Application No. PCT/EP2021/076730 Origo Biopharma, S. L., International filing date of Sep. 29, 2021, date of mailing Jan. 26, 2022, 10 pgs.
Sawyer, J. Scott, et al. "Synthesis and Activity of New Aryl- and Heteroaryl-Substituted Pyrazole Inhibitors of the Transforming Growth Factor-β Type I Receptor Kinase Domain." Journal of Medicinal Chemistry, vol. 46, No. 19, 2003, pp. 3953-3956.
Sawyer, J. Scott, et al. "Synthesis and Activity of New Aryl- and Heteroaryl-Substituted Pyrazole Inhibitors of the Transforming Growth Factor-β Type I Receptor Kinase Domain." Journal of Medicinal Chemistry, vol. 46, No. 19, 2003, pp. 3953-3956.
Zhu, Wen-Jing, et al. "Design, Synthesis, and Antifibrosis Evaluation of 4-(Benzo-[c][1,2,5]Thiadiazol-5-YI)-3(5)-(6-Methyl-Pyridin-2-YI)Pyrazole and 3(5)-(6-Methylpyridin-2-YI)-4-(Thieno-[3,2,-c]Pyridin-2-YI)Pyrazole Derivatives." European Journal of Medicinal Chemistry, vol. 180, 2019, pp. 15-27.

* cited by examiner

2-(3-PYRIDIN-2-YL-4-QUINOLIN-4-YL-PYRAZOL-1-YL)- ACETAMIDE DERIVATIVES AS INHIBITORS OF TRANSFORMING GROWTH FACTOR-BETA RECEPTOR I/ALK5

FIELD OF THE INVENTION

The present invention relates to novel 2-(3-pyridin-2-yl-4-quinolin-4-yl-pyrazol-1-yl)-acetamide derivatives as potent inhibitors of transforming growth factor-β receptor I, (also named activin receptor-like kinase 5) (TGFβRI)/ALK5.

Other objectives of the present invention are to provide a procedure for preparing these compounds; pharmaceutical compositions comprising an effective amount of these compounds; the use of the compounds for manufacturing a medicament for the treatment of pathological conditions or diseases that can improve by inhibition of transforming growth factor-β receptor I (TGFβRI)/ALK5, such as respiratory diseases including idiopathic pulmonary fibrosis, asthma, COPD and lung cancer, and dermal and ocular fibrotic conditions.

STATE OF THE ART

Transforming growth factor-β (TGF-β) belongs to the TGF-β superfamily, which consists of TGF-β1, TGF-β2, TGF-β3, among other proteins. TGF-β is involved in many cellular processes, including cell proliferation, cell migration, invasion, epithelial-mesenchymal transition, extracellular matrix production, and immune suppression. TGF-β and its receptors are often chronically over expressed in various human diseases, including cancer, inflammation, tissue fibrosis, and autoimmunity. Therefore, blockade of TGF-β signalling pathway is considered an attractive target for drug development. (Heldin C H, et al, *Signalling Receptors for TGF-b Family Members, Cold Spring Harb Perspect Biol,* 2016).

TGF-β signals via two related transmembrane type I and type II serine/threonine kinase receptors. Following TGF-β binding to the constitutively active type II receptor, the type I receptor (also called activin receptor-like kinase 5 (ALK5)) is phosphorylated and creates a binding site for Smad2 and Smad3 proteins, which are further phosphorylated. Phosphorylated Smad2/Smad3 proteins form a heteromeric complex with Smad4, which translocate into the nucleus, assembles with specific DNA-binding cofactors and co-modulators, and binds to the promoters of TGF-β target genes involved in cell differentiation, proliferation, apoptosis, migration, and extracellular matrix production. (Akhurst R J, et al, *Targeting the TGFβ signalling pathway in disease*, Nature/Reviews, October 2012, VOLUME 11).

In most cell types, activin receptor-like kinase 5-ALK5 (also known as TGFβR1) is the predominant TGFβ receptor I that is activated by TGF-β through TGFβ receptor II. This interaction requires both extracellular and intracellular domains for signal transduction.

ALK5 and TGFβ receptor II proteins can also form active heterooligomeric complexes in the absence of ligand. These complexes are able to transduce basal signals when both receptors are co-expressed because of their intrinsic affinity for interaction. (Bierie B et al, TGF-β: the molecular Jekyll and Hyde of cancer, Nature Reviews, Cancer, Volume 6, July 2006).

The functional TGFβRII-TGFβRI (ALK5) heteromeric signalling complex is commonly associated with human cancer, and it regulates the activation of downstream Smad-dependent and Smad-independent pathways. In fact, many studies have identified mutations in components that are associated with the TGF-β pathway, and which correlate with cancer occurrence and prognosis in many human tissues. The over expression of TGF-β1 has been associated with breast, colon, oesophageal, gastric, hepatocellular, lung and pancreatic cancer. Importantly, the overexpression of TGF-β in human cancer correlates with tumour progression, metastasis, angiogenesis and poor prognostic outcome.

The transforming growth factor (TGF-β) cytokines play a central role in development and progression of chronic respiratory diseases. TGF-β overexpression in chronic inflammation, remodelling, fibrotic process, and susceptibility to viral infection is established in the most prevalent chronic respiratory diseases including pulmonary fibrosis, asthma, COPD and lung cancer.

Idiopathic Pulmonary Fibrosis

Pulmonary fibrosis is a chronic and progressive lung disease, in which repeated wound and repair processes lead to irreversible structural alterations and tissue stiffening. Pathophysiological steps include alveolar epithelial damage by extrinsic irritants, fibroblast activation and persistent fibrotic reaction. Differentiation of lung fibroblasts into myofibroblasts is a key step in the development of tissue fibrosis. TGF-β is the most potent factor for the induction of myofibroblast differentiation and increased expression of this factor has been reported in fibrotic lungs. The major cellular sources of TGF-β in pulmonary fibrosis have been shown to be alveolar macrophages and metaplastic type II alveolar epithelial cells. TGF-β induces molecules regulators of small GTPases and promotes lung fibrosis by suppressing production of anti-fibrotic molecules such as hepatocyte growth factor and prostaglandin E2. Furthermore, TGF-β inhibits alveolar epithelial cell growth and repair, so it is a key player in fibrotic processes, acting on both fibroblasts and alveolar epithelial cells (Saito A. et al, *TGF-β Signaling in Lung Health and Disease*, Int. J. Mol. Sci. 2018, 19, 2460).

Extensive evidence suggests that the canonical ALK5/Smad3 pathway is critically involved in the pathogenesis of fibrosis in many tissues. Oral administration of a small molecular weight selective inhibitor of the kinase activity of ALK5 inhibited fibrogenesis in a rat model of progressive TGF-β1-induced pulmonary fibrosis. Furthermore, Smad3 null mice exhibit attenuated fibrosis in a wide range of experimental models and are resistant to bleomycin-induced pulmonary fibrosis. (Biernacka, A et al, *TGF-β signalling in fibrosis*, Growth Factors. 2011 October; 29(5): 196-202).

Asthma and COPD

Asthma and chronic obstructive pulmonary disease (COPD) exacerbations are commonly associated with viral infection. The ensuing airway inflammation is resistant to the anti-inflammatory actions of glucocorticoids (GCs). Viral infection elicits transforming growth factor-β (TGF-β) activity, a growth factor impairing GC action in human airway epithelial cells through the activation of activin-like kinase 5 (ALK5). A study examined the contribution of TGF-β activity to the GC-resistance caused by viral infection, demonstrating that GC impairment was attenuated by the selective ALK5/TGFβRI inhibitor, SB431542, and prevented by the therapeutic agent, tranilast, which reduced TGF-β activity associated with viral infection. This study showed that viral-induced glucocorticoid-insensitivity is partially mediated by activation of endogenous TGF-β. (Xia Y C et al, *Glucocorticoid Insensitivity in Virally Infected Airway Epithelial Cells Is Dependent on Transforming*

*Growth Factor-β Activity*, PLoS Pathog, Jan. 3, 2017, 13(1), doi:10.1371/journal.ppat.1006138).

Particularly, asthma is characterized by chronic airway inflammation and hyperresponsiveness mediated by T-helper type 2 (Th2) cells and several cytokines and interleukins. These cytokines cause chronic inflammation, pulmonary eosinophilia, mucus cell hyperplasia, smooth muscle contraction and airway remodelling. In addition to Th2 cells, Th17 cells that secrete IL-17A and IL-17F also participate in the development of allergic airway inflammation. The importance of TGF-β signaling in the pathogenesis of asthma has been illustrated by genome-wide association studies. It has been demonstrated that TGF-β concentration in bronchoalveolar lavage fluid is elevated in atopic asthma and TGF-β expression is increased in bronchial specimens of asthmatic patients. The pathological role of TGF-β in asthma is not restricted to airway remodelling, and its effect on the immune response is thought to be more important than previously recognized. (Saito A. et al, *TGF-β Signalling in Lung Health and Disease*, Int. J. Mol. Sci. 2018, 19, 2460).

In the asthmatic airway, immunohistochemical localization with TGF-β1 or pan-specific antibodies indicate that TGF-β is increased and associated predominantly with submucosal and inflammatory cells, including fibroblasts, smooth muscle cells, eosinophils, macrophages and the connective tissue of the airway, with variable expression in epithelial cells. Increased expression of TGF-β in the asthmatic airway has been attributed predominantly to increases in the number of eosinophils and macrophages.

Consistent with studies showing increased expression of TGF-β in asthmatic airways, there is also evidence for increased TGF-β signalling with increased phosphorylated Smad2 and decreased Smad7 immunoreactivity. Furthermore, studies in animal models of airway remodelling have shown that bronchoalveolar lavage levels of TGF-β1 are increased, together with evidence of activation of TGF-β/Smad signalling.

In addition, evidence from animal models suggests that airway remodelling may be prevented or reversed using agents which target TGF-β. Therefore, modulation of TGF-βs or their activity represent a potential therapeutic target for asthma. (Howell, J. E. et al, *TGF-β: Its Role in Asthma and Therapeutic Potential*, Current Drug Targets, 2006, 7, 547-565).

On the other hand, chronic obstructive pulmonary disease (COPD) is characterized by irreversible airflow obstruction, small airway inflammation, and destruction of alveolar architecture with airspace enlargement. Several studies have demonstrated impaired TGF-β1 signalling in patients with COPD. Investigators have identified increased TGF-β1 in the airway epithelium of smokers and those with COPD as well as decreased expression of inhibitory Smads. Similar to the role of TGF-β in pulmonary fibrosis, in COPD patients TGF-β promotes fibrotic airway remodelling, which can further contribute to diminished lung function. Some of the increases in TGF-β1 in the airway epithelium of COPD patients may be a direct response to cigarette smoke, the most significant risk factor for development of this disease state (Aschner, Y. et al, *Transforming Growth Factor-β: Master Regulator of the Respiratory System in Health and Disease*, American Journal of Respiratory Cell and Molecular Biology, 2016. 54(5), 647-655).

Lung Cancer

Lung cancer is the leading cause of cancer-related mortality worldwide. Non-small cell lung cancer (NSCLC) comprises the majority of lung cancers, which include the histological subtypes of adenocarcinoma and squamous cell carcinoma. Higher TGF-β expression levels are associated with lymph node metastasis and tumour angiogenesis in NSCLC and tumour cells established from NSCLC express TGF-β ligands. It is widely believed that TGF-β plays dual roles during tumour progression, suppressing epithelial cell proliferation and acting as a tumour suppressor in the early stage of tumorigenesis; loss-of-function mutations in TGF-β signalling components have been identified in several cancer types.

Besides its direct effect on cancer cells, TGF-β facilitates invasion and metastatic spread through reciprocal interactions between cancer cells and the tumour stromal microenvironment. TGF-β orchestrates the development of tumour stroma and promotes angiogenesis, immune evasion, and remodelling. The stromal reaction presumably mediated by TGF-β is associated with poor prognosis in resected lung adenocarcinomas (Saito A et al, *TGF-β Signalling in Lung Health and Disease*, Int. J. Mol. Sci. 2018, 19, 2460).

Viral Infection

Other study has shown that concomitant viral infection on the background of pre-existing bleomycin induced fibrosis in mice leads to prominent and extensive inflammatory changes that are reminiscent of ground-glass opacities and consolidation reported in individuals with AE-IPF. Blocking TGFβ-ALK5 signalling by therapeutic dosing with the potent and selective ALK5 antagonist SB525334 was highly effective in blocking the progression of fibrosis in the single-hit bleomycin-alone injured mouse model, but the anti-fibrotic effect of this agent was dramatically reduced in the presence of concomitant viral infection. In contrast, this inhibitor was highly effective in attenuating extensive inflammatory cell infiltration associated with concomitant viral infection and it enhanced the antiviral cytokine response.

These studies highlight the pleiotropic nature of the TGFβ-ALK5 signalling axis in pulmonary fibrosis, with different outcomes in response to ALK5 inhibition depending on the presence of viral infection. These findings thus raise important considerations for the future targeting of TGFβ signalling in the context of pulmonary fibrosis: different outcomes on fibrotic progression are expected in stable IPF versus Acute Exacerbation-IPF associated with viral infection. (Smoktunowicz, N et al, *The anti-fibrotic effect of inhibition of TGFβ-ALK5 signalling in experimental pulmonary fibrosis in mice is attenuated in the presence of concurrent γ-herpesvirus infection*, Dis Model Mech. 2015 Sep. 1; 8(9): 1129-1139).

It has demonstrated that both innate and adaptive TGF-β immune signalling led to increased HSV-1 latency and reactivation. The coordinated activity of TGF-β signalling in these two immune compartments seems to be of essential importance in regulating the latent phase of viral infection. If these results extrapolate to clinical HSV-1 infection, then blocking TGF-β signaling in immune cells may represent an important new therapeutic approach to virus-associated disease. (Allen, S J et al, *Adaptive and Innate Transforming Growth Factor β Signalling Impact Herpes Simplex Virus 1 Latency and Reactivation*, Journal of Virology, November 2011, p. 11448-11456).

Severe acute respiratory syndrome (SARS)-associated coronavirus (SARS-CoV) is the causative agent of SARS outbreak in 2003. SARS-CoV infection induces severe respiratory illnesses, such as bronchial epithelial denudation, loss of cilia, multinucleated syncytial cells, squamous metaplasia and transendothelial migration of monocytes/macrophages and neutrophils into lung tissue. SARS-CoV triggers a pro-inflammatory cytokine storm that links with pulmonary fibrosis of SARS patients. Near 20% of SARS patients recovered still have lung fibrosis 9 months post infection.

SARS coronavirus (SARS-CoV) papain-like protease (PLpro) has been identified in TGF-β1 up-regulation in human promonocytes SARS-CoV PLpro inducing TGF-β 1 mediated pro-fibrotic responses in human lung epithelial cells and mouse lung tissues, in accordance with the previous report in that PLpro up-regulated TGF-β 1 and its associated genes such as glial fibrillary acidic protein (GFAP) and vimentin. Except SARS-CoV nucleocapsid, PLpro was identified to generate the TGF-β 1 production that linked to activate the pro-fibrotic responses. Among SARS-CoV-induced cytokines, TGF-β 1 could be associated with the induction of lung fibrosis. Therefore, SARS-CoV PLpro plays an important role in the TGF-β 1-mediated pulmonary fibrosis of SARS pathogenesis. (Li S W, et al, *SARS coronavirus papain-like protease induces Egr*-1-*dependent up-regulation of TGF*-β1 *via ROS/p*38 *MAPK/STAT*3 *pathway*, Sci Rep. 2016 May 13; 6: 25754).

Antifibrotic therapies that are available or in development could have value in preventing severe other coronavirus infections, like COVID-19, in patients with IPF, and might have a role in preventing fibrosis after SARS-CoV-2 infection. Therefore, it is possible that antifibrotic therapies developed for chronic fibrotic lung diseases using bleomycin models might actually be beneficial in COVID-19, both in the acute phase of the illness and in preventing long-term complications. (George, P M et al, *Pulmonary fibrosis and COVID*-19*: the potential role for antifibrotic therapy*, www.thelancet.com/respiratory Published online May 15, 2020).

A major target for antifibrotic therapies is the TGF-β pathway. There are a number of drugs in development that target various molecules in this pathway, including those against av36 integrin (BG00011 [Biogen, Cambridge, MA, USA]; PLN-74809 [Pliant Therapeutics, San Francisco, CA, USA]) and galectins (TD139 [Galecto Biotech, Copenhagen, Denmark]). There are some experimental data to support the use of these three drugs in viral induced lung injury.

Eye Diseases

Transforming growth factor-β (TGF-β) may play a role in the pathogenesis of primary open-angle glaucoma (POAG). TGF-β has been implicated in the pathogenesis of POAG, and potential areas for TGF-β targeting include production, activation, downstream signalling and local regulation. Elevated levels of TGF-β are found in the aqueous humour and in reactive optic nerve astrocytes in patients with glaucoma. Although recent research has revealed many unknowns, a deeper understanding of TGF-β's cellular signalling pathways is necessary for designing potential TGF-β intervention strategies. (Wang, J. et al, Targeting Transforming Growth Factor-b Signalling in Primary Open-Angle Glaucoma, J Glaucoma 2017; 26:390-395).

Eye diseases associated with a fibroproliferative condition include retinal reattachment surgery accompanying proliferative vitreoretinopathy, cataract extraction with intraocular lens implantation, and post-glaucoma drainage surgery are associated with TGF-31 overproduction.

The authors of the present invention have developed new ester derivatives conveniently substituted as potent and selective inhibitors of TGF-β signalling pathway, particularly as inhibitors of transforming growth factor-β receptor 1/activin-like kinase 5 (TGFβRI/ALK5).

SUMMARY OF THE INVENTION

In one of its aspects (aspect 1), the present invention refers to ester derivatives conveniently substituted of formula (I):

(I)

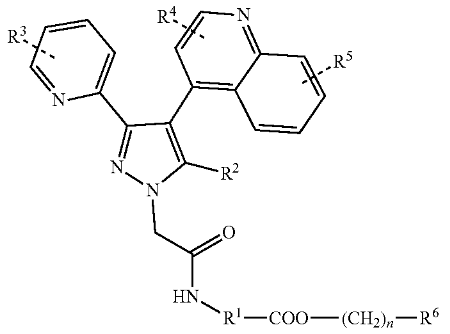

wherein:

$R^1$ represents a group selected from:

a) phenyl ring unsubstituted or substituted by 1 or 2 groups selected from halogen atom, linear or branched $C_1$-$C_3$ haloalkyl, linear or branched $C_1$-$C_3$ alkyl, linear or branched $C_1$-$C_3$ alkoxy, cyano group and hydroxy group, b) 5- or 6-membered heteroaryl ring unsubstituted or substituted by 1 or 2 groups selected from halogen atom, linear or branched $C_1$-$C_3$ haloalkyl, linear or branched $C_1$-$C_3$ alkyl, linear or branched $C_1$-$C_3$ alkoxy, cyano group and hydroxy group, $R^2$ is a group selected from:

a) hydrogen atom, b) linear or branched $C_1$-$C_3$ alkyl optionally substituted by 1, 2 or 3 halogen atoms, $R^3$ represents a group selected from:

a) hydrogen atom, b) linear or branched $C_1$-$C_3$ alkyl optionally substituted by 1, 2 or 3 halogen atoms, c) halogen atom, $R^4$ and $R^5$ represent independently a group selected from:

a) hydrogen atom, b) linear or branched $C_1$-$C_3$ alkyl optionally substituted by 1, 2 or 3 halogen atoms, c) halogen atom, n is an integer from 0 to 3, $R^6$ represents a group selected from the group consisting of:

a) —$N(R^7)(R^8)$, wherein $R^7$ and $R^3$ represent independently a linear or branched Cr $C_6$ alkyl group or a hydrogen atom, and b) saturated 4- to 10-membered, monocyclic or bicyclic, nitrogen-containing heterocyclyl optionally comprising another heteroatom selected from the group consisting of oxygen and nitrogen, said heterocyclyl being optionally substituted by a group selected from $C_1$-$C_3$ alkyl group, and pharmaceutically acceptable salts thereof.

In a second aspect the present invention relates to processes for the preparation of the compounds of aspect 1.

In a third aspect the present invention relates to pharmaceutical compositions comprising a compound of aspect 1 and a pharmaceutical acceptable diluent or carrier.

In a fourth aspect the present invention relates to pharmaceutical compositions according to the third aspect described above which further comprise a therapeutically effective amount of a therapeutic agent selected from agent useful for the treatment of respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In a fifth aspect the present invention relates to the use of the compound of aspect 1 in the manufacture of a medicament for the treatment of a disease or pathological condition that can be ameliorated by inhibition of transforming growth factor-β receptor I (TGFβRI)/ALK5, such as respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In a sixth aspect the present invention relates to methods for the treatment of diseases that can be ameliorated by inhibition of transforming growth factor-β receptor I (TGFβRI)/ALK5, such as respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In a seventh aspect the present invention relates to a combination product of the compound of the first aspect described above with one more therapeutic agent known to be useful in the treatment of respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In an eighth aspect the present invention relates to the compound of aspect 1 for use as a medicament.

In a ninth aspect the present invention relates to the compound of aspect 1 for use in the treatment of a disease or pathological condition that can be ameliorated by inhibition of transforming growth factor-β receptor I (TGFβRI)/ALK5, such as respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

As it is said before, ester derivatives of the present invention are useful in the treatment or prevention of diseases known to be susceptible to amelioration by treatment with inhibitor of transforming growth factor-β receptor I (TGFβRI)/ALK5, such as respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

Accordingly, the derivatives of the present invention and pharmaceutically acceptable salts thereof, and pharmaceutical compositions comprising such compounds and/or salts thereof, may be used in a method of treatment of pathological conditions or disease of human body which comprises administering to a subject in need of said treatment, an effective amount of the ester derivatives of the invention or a pharmaceutically acceptable salt thereof.

As used herein, the term $C_a$-$C_b$ alkyl includes linear or branched radicals, having from a to b carbon atoms. Preferred radicals include 1 to 4 carbon atoms. Examples of linear or branched alkyl groups are methyl, ethyl, n-propyl, iso-propyl, n-butyl, i-butyl, sec-butyl, tert-butyl, pentyl and hexyl.

As used herein, the term linear or branched $C_a$-$C_b$ alkoxy is used to designate radicals which contain linear or branched $C_a$-$C_b$ alkyl radicals linked to an oxygen atom ($C_xH_{2x+1}$—O—). Preferred alkoxy radicals include for example, methoxy, ethoxy, n-propoxy, i-propoxy.

As used herein, the term 5- or 6-membered heteroaryl ring is used to designate unsaturated aromatic ring systems having 5 or 6 members in the ring system selected from the group consisting of C, N, O and S wherein at least one of the members is one of N, O, and S. Said radicals may optionally be substituted by 1 or 2 groups selected from halogen atom, linear or branched $C_1$-$C_3$ haloalkyl, linear or branched $C_1$-$C_3$ alkyl, linear or branched $C_1$-$C_3$ alkoxy, cyano group and hydroxy group. The preferred radicals are optionally substituted pyridinyl, pyrazolyl and thiazolyl ring. When a heteroaryl radical carries 2 or more substituents, the substituents may be the same or different.

As used herein, the term "saturated 4- to 10-membered, monocyclic or bicyclic, nitrogen-containing heterocyclyl" is used to designate ring system which may contain one or two cycles wherein said one or two cycles have in total 4 to 10 members wherein at least one of said members is a nitrogen atom. When the ring system has two cycles each cycle may have from to 3 to 6 members and the two cycles may share one or more bonds. One example of a two cycles sharing one bond is 1-azabicyclo[2.2.0]hexane, an example of two cycles sharing two bonds is 1-azabicyclo[2.2.1]heptane and an example of two cycles sharing three bonds is 1-azabicyclo[2.2.2]octane. Examples of monocyclic nitrogen-containing heterocyclyl groups are piperidinyl, morpholinyl, piperazinyl, 4-methyl-piperazinyl, pyrrolidinyl, azetidinyl and aziridinyl. Examples of bicyclic nitrogen-containing heterocyclyl groups are 1-azabicyclo[2.2.0]hexanyl, 1-azabicyclo [2.2.1]heptanyl and decahydroquinolinyl. Said radicals may optionally be substituted by 1, 2 or 3 groups selected from linear or branched $C_1$-$C_3$ alkyl and hydroxy group. The preferred radicals are optionally substituted piperazinyl, piperidinyl, morpholinyl and 1-azabicyclo[2.2.2]octanyl (quinuclidinyl) group.

As used herein, the term halogen atom includes chlorine, fluorine, bromine and iodine atoms, preferably fluorine, chlorine and bromine atoms. The term halo, when used as a prefix, has the same meaning. As a mere example haloalkyl means an alkyl substituted by one or more halogen atoms.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different.

As used herein, the term pharmaceutically acceptable salt is used to designate salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

Other preferred salts according to the invention are quaternary ammonium compounds wherein an equivalent of an anion ($X^{-n}$) is associated with the positive charge of the N atom. $X^{-n}$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulfonate and p-toluenesulphonate. $X^{-n}$ is preferably an anion selected from chloride, bromide, iodide, sulphate, nitrate, acetate, maleate, oxalate, succinate or trifluoroacetate. More preferably, $X^{-n}$ is chloride, bromide, trifluoroacetate or methanesulfonate.

According to one embodiment of the present invention in the compounds of formula (I), $R^1$ represents a phenyl ring unsubstituted or substituted by 1 or 2 halogen atoms. In a preferred embodiment, $R^1$ represents a phenyl ring substituted by 1 or 2 halogen atoms.

In a more preferred embodiment, $R^1$ represents a phenyl ring substituted by one halogen atom.

According to one embodiment of the present invention in the compounds of formula (I), $R^2$ represents a hydrogen atom.

According to one embodiment of the present invention in the compounds of formula (I), $R^3$ represents a group selected from a hydrogen atom and linear or branched $C_1$-$C_3$ alkyl unsubstituted. In a preferred embodiment, $R^3$ represents a methyl group.

According to one embodiment of the present invention in the compounds of formula (I), $R^4$ represents a hydrogen atom.

According to one embodiment of the present invention in the compounds of formula (I), $R^5$ represents a hydrogen atom.

According to one embodiment of the present invention in the compounds of formula (I), n is an integer from 0 to 2. In a preferred embodiment, n is an integer from 1 to 2.

According to one embodiment of the present invention in the compounds of formula (I), $R^6$ represents a —$N(R^7)(R^8)$ group, wherein $R^7$ and $R^3$ represent independently a group selected from linear $C_1$-$C_3$ alkyl group and hydrogen atom.

According to one embodiment of the present invention in the compounds of formula (I), $R^6$ represents a saturated 4- to 6-membered, monocyclic, nitrogen-containing heterocyclyl comprising a nitrogen atom attached to the —$(CH_2)$n- group and optionally one further nitrogen atom which may be substituted by a methyl group. In a preferred embodiment, $R^6$ represents a saturated 6-membered heterocyclic group containing 1 or 2 nitrogen atoms, optionally substituted by a methyl group.

In a more preferred embodiment, $R^6$ represents a group selected from piperazinyl and piperidinyl group.

According to one embodiment of the present invention in the compounds of formula (I), $R^6$ represents 1-aza-bicyclo [2.2.2]octanyl group.

According to one embodiment of the present invention in the compounds of formula (I), $R^2$, $R^4$ and $R^5$ represent hydrogen atom.

According to one embodiment of the present invention in the compounds of formula (I), n is an integer from 1 to 2 and $R^6$ represents a —$N(R^7)(R^8)$ group, preferably wherein $R^7$ and $R^3$ represent independently a group selected from linear $C_1$-$C_3$ alkyl group and hydrogen atom.

According to one embodiment of the present invention in the compounds of formula (I), $R^2$, $R^4$ and $R^5$ represent hydrogen atom, $R^3$ represents linear $C_1$-$C_3$ alkyl, $R^1$ represents a phenyl ring substituted by 1 or 2 halogen atoms, n is an integer from 0 to 2 and $R^6$ represents a group selected from the group consisting of:

a) —$N(R^7)(R^8)$, wherein $R^7$ and $R^3$ are selected from linear $C_1$-$C_3$ alkyl group and hydrogen atom,
b) a saturated 6-membered heterocyclic group containing 1 or 2 nitrogen atoms, optionally substituted by a methyl group,
c) 1-aza-bicyclo[2.2.2]octanyl.

Particular individual compounds of the present invention include:

2-(dimethylamino)ethyl 3-fluoro-5-(2-(3-(6-methylpyridin-2-yl)-4-(quinolin-4-yl)-1H-pyrazol-1-yl)acetamido)benzoate
2-(dimethylamino)ethyl 5-(2-(3-(6-methylpyridin-2-yl)-4-(quinolin-4-yl)-1H-pyrazol-1-yl)acetamido)nicotinate
2-(dimethylamino)ethyl 6-(2-(3-(6-methylpyridin-2-yl)-4-(quinolin-4-yl)-1H-pyrazol-1-yl)acetamido)nicotinate
2-morpholinoethyl 3-fluoro-5-(2-(3-(6-methylpyridin-2-yl)-4-(quinolin-4-yl)-1H-pyrazol-1-yl)acetamido)benzoate
2-(dimethylamino)ethyl 5-(2-(3-(6-methylpyridin-2-yl)-4-(quinolin-4-yl)-1H-pyrazol-1-yl)acetamido)picolinate
2-(4-methylpiperazin-1-yl)ethyl 3-fluoro-5-(2-(3-(6-methylpyridin-2-yl)-4-(quinolin-4-yl)-1H-pyrazol-1-yl)acetamido)benzoate
2-(diethylamino)ethyl 3-fluoro-5-(2-(3-(6-methylpyridin-2-yl)-4-(quinolin-4-yl)-1H-pyrazol-1-yl)acetamido)benzoate 1-methylpiperidin-4-yl 3-fluoro-5-(2-(3-(6-methylpyridin-2-yl)-4-(quinolin-4-yl)-1H-pyrazol-1-yl)acetamido)benzoate (1-methylpiperidin-4-yl)methyl 3-fluoro-5-(2-(3-(6-methylpyridin-2-yl)-4-(quinolin-4-yl)-1H-pyrazol-1-yl)acetamido)benzoate (R)-quinuclidin-3-yl 3-fluoro-5-(2-(3-(6-methylpyridin-2-yl)-4-(quinolin-4-yl)-1H-pyrazol-1-yl)acetamido)benzoate (S)-quinuclidin-3-yl 3-fluoro-5-(2-(3-(6-methylpyridin-2-yl)-4-(quinolin-4-yl)-1H-pyrazol-1-yl)acetamido)benzoate quinuclidin-4-yl 3-fluoro-5-(2-(3-(6-methylpyridin-2-yl)-4-(quinolin-4-yl)-1H-pyrazol-1-yl)acetamido)benzoate 2-(azetidin-1-yl)ethyl 3-fluoro-5-(2-(3-(6-methylpyridin-2-yl)-4-(quinolin-4-yl)-1H-pyrazol-1-yl)acetamido)benzoate 2-(aziridin-1-yl)ethyl 3-fluoro-5-(2-(3-(6-methylpyridin-2-yl)-4-(quinolin-4-yl)-1H-pyrazol-1-yl)acetamido)benzoate 2-(methylamino)ethyl 3-fluoro-5-(2-(3-(6-methylpyridin-2-yl)-4-(quinolin-4-yl)-1H-pyrazol-1-yl)acetamido)benzoate 2-aminoethyl 3-fluoro-5-(2-(3-(6-methylpyridin-2-yl)-4-(quinolin-4-yl)-1H-pyrazol-1-yl)acetamido)benzoate 2-(ethylamino)ethyl 3-fluoro-5-(2-(3-(6-methylpyridin-2-yl)-4-(quinolin-4-yl)-1H-pyrazol-1-yl)acetamido)benzoate 2-(isopropylamino)ethyl 3-fluoro-5-(2-(3-(6-methylpyridin-2-yl)-4-(quinolin-4-yl)-1H-pyrazol-1-yl)acetamido)benzoate 2-(piperazin-1-yl)ethyl 3-fluoro-5-(2-(3-(6-methylpyridin-2-yl)-4-(quinolin-4-yl)-1H-pyrazol-1-yl)acetamido)benzoate piperidin-4-ylmethyl 3-fluoro-5-(2-(3-(6-methylpyridin-2-yl)-4-(quinolin-4-yl)-1H-pyrazol-1-yl)acetamido)benzoate piperidin-4-yl 3-fluoro-5-(2-(3-(6-methylpyridin-2-yl)-4-(quinolin-4-yl)-1H-pyrazol-1-yl)acetamido)benzoate and pharmaceutically acceptable salts thereof.

The compounds of the present invention can be prepared by using the procedures described below. To facilitate the description of the procedures, concrete examples have been used but they do not restrict in any way the scope of the present invention. The synthesis of compound of formula (I) is outlined in Scheme 1

Scheme 1

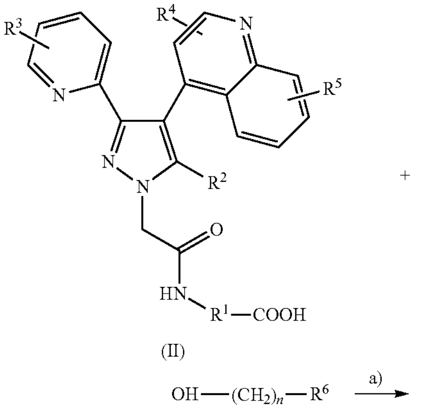

(II)

(III)

-continued

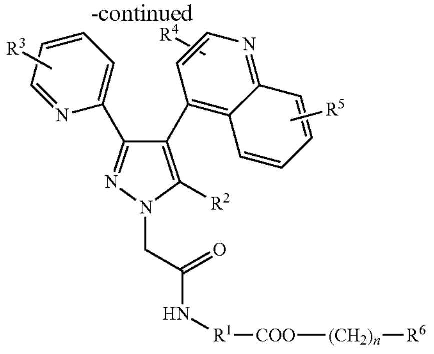

(I)

The amide formation reaction a) can be undertaken in one or two steps following one of the following alternative conditions:

Alternative 1: Step 1. $SOCl_2$, $CH_2Cl_2$, ref. Step 2. HO—$(CH_2)_n$—$R^6$, $CH_2Cl_2$, DIPEA, RT Alternative 2: Step 1. $SOCl_2$, $CH_2Cl_2$, ref. Step 2. HO—$(CH_2)_n$—$R^6$, $CH_2Cl_2$, RT Alternative 3: Step 1. HO—$(CH_2)_n$—$R^6$, HATU, DIPEA, DMF, RT Alternative 4: Step 1. HO—$(CH_2)_n$—$R^6$, HOBT, EDCl, DIPEA, DMF, RT.

In the case that the group $R^6$ represents an amine group (—$N(R^7)(R^8)$), wherein at least one of $R^7$ and $R^3$ is a hydrogen atom, said amine group is protected with BOC (See Scheme 7) before the above-mentioned reaction and the protecting Boc group is cleaved after the above mentioned reaction with HCl-dioxane, dioxane, 0° C. to RT.

The carboxylic esters of general formula (I) are prepared from 2-(2-(3-(pyridin-2-yl)-4-(quinolin-4-yl)-1H-pyrazol-1-yl)acetamido)acetic acid derivatives (II) by esterification with the suitable alcohols (III) under acidic conditions (Lee, J.-J. et al., *Fluorescent Chemosensor for Chloroalkanes*, Organic Letters, 10(9), 1735-1738; 2008) or in the presence of a coupling reagent system (Wang, X. et al., *Metal-Free Etherification of Aryl Methyl Ether Derivatives by C-OMe Bond Cleavage*, Organic Letters, 20(14), 4267-4272; 2018).

In those compounds in which $R^7$ or $R^3$ represents a hydrogen group, a deprotection of the N-Boc protected precursor is carried out under acid conditions.

Compounds of general formula (II) are prepared in several stages from 4-(3-(pyridin-2-yl)-1H-pyrazol-4-yl)quinoline derivatives (IV) by deprotonation followed by reaction with the corresponding bromoacetamide (V) as is indicated in Scheme 2 and described in WO2009123316 A1 which is incorporated by reference.

Scheme 2

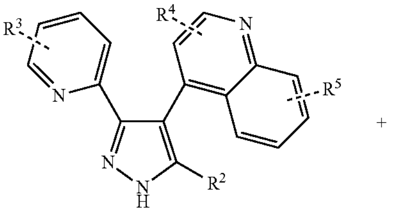

(IV)

-continued

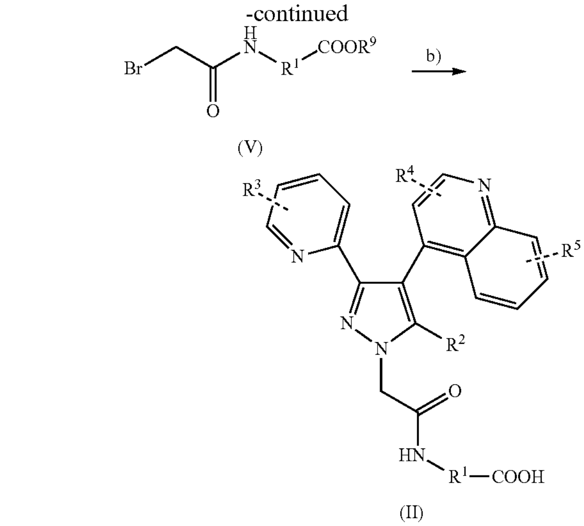

(V)

(II)

$R^9$ = H or tBu

Reagents and conditions:

Reaction b) Step 1. NaH, THF, DMF, 0° C. to RT.

Compounds in which $R^9$ = tButyl group: Step 2. HCl•dioxane, dioxane, ref. or RT.

Some 4-(3-(pyridin-2-yl)-1H-pyrazol-4-yl)quinoline derivatives (IV) are commercially available and others (in which $R^2$ is H) can be prepared in several steps as is indicated in Scheme 3 and described in WO2004026302 A1 which is incorporated by reference.

Scheme 4

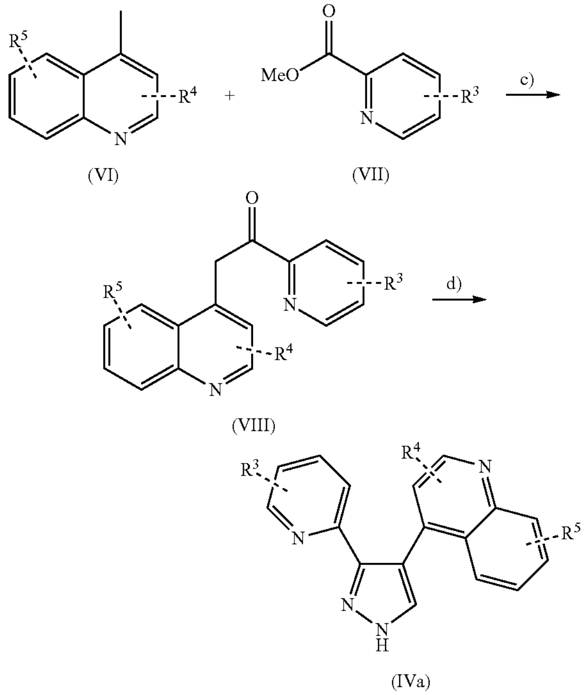

(VI) (VII)

(VIII)

(IVa)

Reagents and conditions:

Reaction c) LiHMDS, THF, -30° C. to RT.

Reaction d) Compounds in which $R^2$ = H. Step 1. DMF•DMA, AcOH, DMF, 0°C. to RT; Step 2. $N_2H_4$•$H_2O$, 0° C. to RT.

The 4-methylquinoline derivatives (VI) are condensed with ethyl 2-pyridinecarboxylate (VII) in the presence of lithium bis(trimethylsilyl)amides to provide compounds of formula (VIII). The reaction of the derivatives (VIII) with dimethylformamide dimethylacetal affords to non-isolated enamine intermediates, which are cyclised directly by reaction with hydrazine in presence of acetic acid to provide pyrazole derivatives of formula (IVa).

Compounds in which $R^2$ is a linear or branched $C_1$-$C_3$ alkyl optionally substituted by 1, 2 or 3 halogen atoms (IVb) may be prepared according to the following scheme 4:

Scheme 4

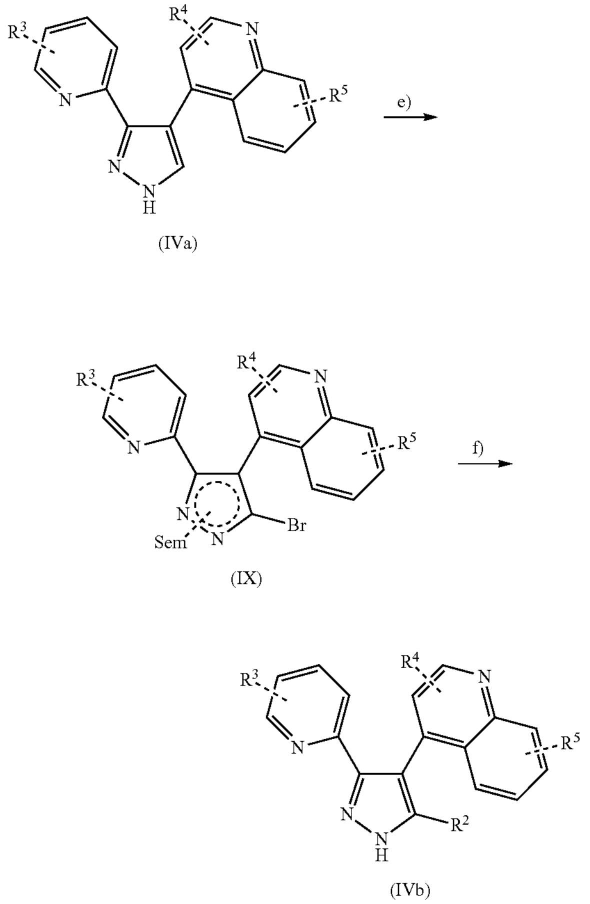

(IVa)

(IX)

(IVb)

Reagents and conditions:

Reaction e): Step 1. NBS, $CH_2Cl_2$, 0° C. Step 2. SemCl, $Cs_2CO_3$, DMF, 0° C.

Reaction f): Step 1. $R^2B(OH)_2$, DMF, $NaHCO_3$, $PdCl_2(PPh_3)_2$ Step 2. $BCl_3$, $SMe_2$, $CH_2Cl_2$, 0° C.

The pyrazole derivatives of formula (IVa) can be halogenated to give the corresponding compounds of formula (IX) with standard halogenation reagents, as succinimide derivatives, after the protection of the nitrogen of the pyrazole ring. A C—C coupling followed of the deprotection of nitrogen of the pyrazole to give derivatives of formula (IVb).

The bromoacetamides the formula (V) are readily synthesized in one stage from commercially available amines (X) by reaction with bromoacetyl bromide the formula (XI) as is indicated in Scheme 5 (Shaw, S. J., et al., Structure-Activity Relationships of 9-Substituted-9-Dihydroerythromycin-Based Motilin Agonists: Optimizing for Potency and Safety, J. Med. Chem., 52, 6851-6859, 2009).

Scheme 5

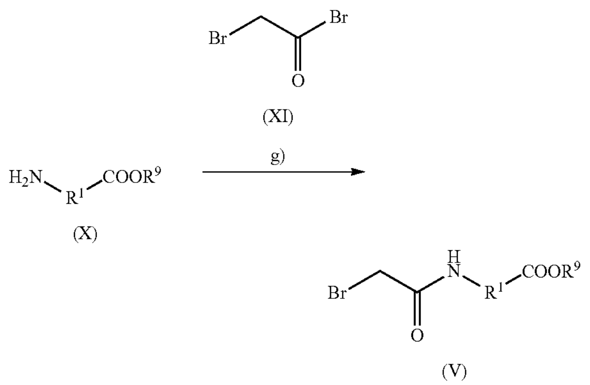

(XI) (X) (V)

Reagents and conditions:
Reaction g) THF, 0° C. to RT or $CH_2Cl_2$, $Et_3N$, 0° C. to RT.

Some amines (X) are commercially available and other can be prepared in few steps as is indicated in the Scheme 6.

Scheme 6

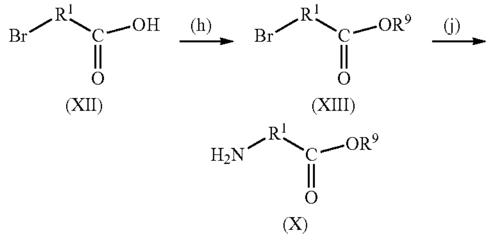

(XII) (XIII) (X)

$R^9 = {}^tBu$ $R^1$ represents a group selected from:

a) phenyl ring unsubstituted or substituted by 1 or 2 groups selected from halogen atom, linear or branched $C_1$-$C_3$ haloalkyl, linear or branched $C_1$-$C_3$ alkyl, linear or branched $C_1$-$C_4$ alkoxy, cyano group and hydroxy group b) 5- or 6-membered heteroaryl ring unsubstituted or substituted by 1 or 2 groups selected from halogen atom, linear or branched $C_1$-$C_3$ haloalkyl, linear or branched $C_1$-$C_3$ alkyl, linear or branched $C_1$-$C_4$ alkoxy, cyano group and hydroxy group.

Reaction h)

$Boc_2O$, DMAP, THF, RT.

Reaction j)

trans-4-hidroxy-L-proline, CuI, $NH_4OH$, DMSO, 80° C.

The esterification of the corresponding acids (XII) by reaction with $Boc_2O$ and a catalytic amount of DMAP (Wright, S. W. et al., Preparation of 2-, 4-, 5-, and 6-aminonicotinic acid tert-butyl esters, J. Heterocyclic Chem, 2, 49, 442-445, 2012) followed by treatment of the resulting ester with ammonium hydroxide in presence of the CuI (Substituted tetrahydroisoquinoline compounds as factor xia inhibitors, WO 2013056034) provided amine derivatives of formula (X).

Protected amines of formula (IIIb), wherein at least one of $R^7$ and/or $R^3$ represent a hydrogen atom, are easily synthesized in one stage from commercially available unprotected amine (IIIa) by treatment with $Boc_2O$ as is indicated in the Scheme 7.

Scheme 7

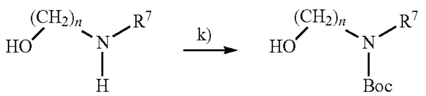

(IIIa) (IIIb)

$R^7$ = H or linear or balanced $C_1$—$C_6$ alkyl group.
Reaction k) $Boc_2O$, $CH_2Cl_2$, 0° C. to RT.

Abbreviations

In the present application are used the following abbreviations, with the corresponding definitions:

AcOH: Acetic Acid
ACVR2B: activin A receptor, type IIB
ALKn: activin receptor-like kinase n
ATP: adenosin triphosphate
$Boc_2O$: tert-butyl dicarbonate
Boc: tert-Butoxycarbonyl
Clint: Intrinsic clearance
DIPEA: N,N-Diisopropylethylamine
DMA: Dimethylacetamide
DMAP: 4-Dimethylaminopyridine
DMF: N,N-Dimethylformamide
DMSO: Dimethyl sulfoxide
EDCl: N-(3-Dimethylaminopropyl)-N'-ethylcarbodiimide)
$Et_3N$: Triethylamine
EtOAc: Ethyl acetate
EtOH: ethanol
FBS: Fetal bovine serum
H: hour
HATU: 1-[Bis(dimethylamino)methylene]-1H-1,2,3-triazolo[4,5-b]pyridinium 3-oxide hexafluorophosphate
HOBT: Hydroxybenzotriazole
HPLC: High-performance liquid chromatography
$^1$H-NMR: Proton nuclear magnetic resonance
$K_2$EDTA: ethylenediaminetetracetic acid dipotassium salt
LC: Liquid chromatography
LiHMDS: Lithium bis(trimethylsilyl)amide
LLOQ: lower limit of quantification
MeCN: Acetonitrile
MeOH: Methanol
Min: minutes
MS: Mass spectroscopy
MTBE: Methyl tert-butyl ether
NBS: N-Bromosuccinimide
NaCMC: Sodium carboxymethyl cellulose
Rt: retention time
RT: room temperature
Sem: 2-(Trimethylsilyl)ethoxymethyl
TGFβ: transforming growth factor-β
THF: Tetrahydrofuran
THF:EtOH: Tetrahydrofuran:ethanol
UPLC: ultra high-performance liquid chromatography
UV: Ultraviolet Pharmacological Activity In Vitro Enzyme Assay: Inhibition of TGFβR-1 Human TGFβR-1 inhibition experiments were carried out in a white 384-microplate low flange (Corning 3572) with ADP-Glo kinase Assay Kit (Promega V9101) and TGFβR-1 Kinase Enzyme System (Promega V4092). Test compounds and standard Galunisertib (Cayman 15312), 50 ng/well TGFβR-1 kinase and 50 μM ATP were added in a final volume of 10 μL/well, using Reaction buffer supplied by kit as assay buffer. The reaction mixture was incubated in gentle shaking for 120 min at RT, after incubation of 10 μL of ADP-Glo Reagent was added and incubated in gentle shaking for 40 min at RT. 20 μL of Kinase Detection Reagent was added and plate was incubated in gentle shaking for 30 min at RT. Luminescence (1000 ms) was measured in Perkin Elmer EnSpire Multimode plate reader.

Results

Table 1 shows the results of assays described below of some compounds of the present invention.

TABLE 1

| Example | Name | $IC_{50}$ |
|---|---|---|
| 1 | 2-(dimethylamino)ethyl 3-fluoro-5-(2-(3-(6-methylpyridin-2-yl)-4-(quinolin-4-yl)-1H-pyrazol-1-yl)acetamido)benzoate | A |
| 2 | 2-(dimethylamino)ethyl 5-(2-(3-(6-methylpyridin-2-yl)-4-(quinolin-4-yl)-1H-pyrazol-1-yl)acetamido)nicotinate | A |
| 3 | 2-(dimethylamino)ethyl 6-(2-(3-(6-methylpyridin-2-yl)-4-(quinolin-4-yl)-1H-pyrazol-1-yl)acetamido)nicotinate | B |
| 4 | 2-morpholinoethyl 3-fluoro-5-(2-(3-(6-methylpyridin-2-yl)-4-(quinolin-4-yl)-1H-pyrazol-1-yl)acetamido)benzoate | B |
| 5 | 2-(dimethylamino)ethyl 5-(2-(3-(6-methylpyridin-2-yl)-4-(quinolin-4-yl)-1H-pyrazol-1-yl)acetamido)picolinate | A |
| 6 | 2-(4-methylpiperazin-1-yl)ethyl 3-fluoro-5-(2-(3-(6-methylpyridin-2-yl)-4-(quinolin-4-yl)-1H-pyrazol-1-yl)acetamido)benzoate | B |
| 7 | 2-(diethylamino)ethyl 3-fluoro-5-(2-(3-(6-methylpyridin-2-yl)-4-(quinolin-4-yl)-1H-pyrazol-1-yl)acetamido)benzoate | B |
| 8 | 1-methylpiperidin-4-yl 3-fluoro-5-(2-(3-(6-methylpyridin-2-yl)-4-(quinolin-4-yl)-1H-pyrazol-1-yl)acetamido)benzoate | B |
| 9 | (1-methylpiperidin-4-yl)methyl 3-fluoro-5-(2-(3-(6-methylpyridin-2-yl)-4-(quinolin-4-yl)-1H-pyrazol-1-yl)acetamido)benzoate | A |
| 10 | (R)-quinuclidin-3-yl 3-fluoro-5-(2-(3-(6-methylpyridin-2-yl)-4-(quinolin-4-yl)-1H-pyrazol-1-yl)acetamido)benzoate | A |
| 11 | (S)-quinuclidin-3-yl 3-fluoro-5-(2-(3-(6-methylpyridin-2-yl)-4-(quinolin-4-yl)-1H-pyrazol-1-yl)acetamido)benzoate | A |
| 12 | quinuclidin-4-yl 3-fluoro-5-(2-(3-(6-methylpyridin-2-yl)-4-(quinolin-4-yl)-1H-pyrazol-1-yl)acetamido)benzoate | A |
| 13 | 2-(azetidin-1-yl)ethyl 3-fluoro-5-(2-(3-(6-methylpyridin-2-yl)-4-(quinolin-4-yl)-1H-pyrazol-1-yl)acetamido)benzoate | B |
| 14 | 2-(aziridin-1-yl)ethyl 3-fluoro-5-(2-(3-(6-methylpyridin-2-yl)-4-(quinolin-4-yl)-1H-pyrazol-1-yl)acetamido)benzoate | A |
| 15 | 2-(methylamino)ethyl 3-fluoro-5-(2-(3-(6-methylpyridin-2-yl)-4-(quinolin-4-yl)-1H-pyrazol-1-yl)acetamido)benzoate | A |
| 16 | 2-aminoethyl 3-fluoro-5-(2-(3-(6-methylpyridin-2-yl)-4-(quinolin-4-yl)-1H-pyrazol-1-yl)acetamido)benzoate | A |
| 17 | 2-(ethylamino)ethyl 3-fluoro-5-(2-(3-(6-methylpyridin-2-yl)-4-(quinolin-4-yl)-1H-pyrazol-1-yl)acetamido)benzoate | A |

TABLE 1-continued

| Example | Name | $IC_{50}$ |
|---|---|---|
| 18 | 2-(isopropylamino)ethyl 3-fluoro-5-(2-(3-(6-methylpyridin-2-yl)-4-(quinolin-4-yl)-1H-pyrazol-1-yl)acetamido)benzoate | A |
| 19 | 2-(piperazin-1-yl)ethyl 3-fluoro-5-(2-(3-(6-methylpyridin-2-yl)-4-(quinolin-4-yl)-1H-pyrazol-1-yl)acetamido)benzoate | A |
| 20 | piperidin-4-ylmethyl 3-fluoro-5-(2-(3-(6-methylpyridin-2-yl)-4-(quinolin-4-yl)-1H-pyrazol-1-yl)acetamido)benzoate | B |
| 21 | piperidin-4-yl 3-fluoro-5-(2-(3-(6-methylpyridin-2-yl)-4-(quinolin-4-yl)-1H-pyrazol-1-yl)acetamido)benzoate | A |

Ranges:
A: $IC_{50}$ =< 100 nM
B: 100 nM < $IC_{50}$ < 250 nM

Determination of the Intracellular TGF-Beta Kinase Activity (ALK-5)

The experiments were carried out in A549 cell line. 30000 cells were seeded in 200 μl of culture medium (Sigma D6046) supplemented with L-Glutamine (Sigma G7513), Penicillin/Streptomycin (Invitrogen 11058) and FBS (Sigma F9665) on a 96 wells microplate (Becton Dickinson 353072). After 16 hours medium was changed to serum free medium. Galunisertib, as inhibitor ligand (Cayman CAY-15312) and recombinant Human TGF-β2 (R&D Systems 302-B2-002) as activator of the ALK-5, were added in their corresponding wells and incubated following the instructions of the Alphascreen AlphaLISA@SureFire® Ultra™ p-SMAD3(Ser423/425) Kit (Perkin Elmer ALSU-PSM3-A500).

Results

Table 2 shows the results of assays described below of some compounds of the present invention.

TABLE 2

| Example | Name | $IC_{50}$ |
|---|---|---|
| 1 | 2-(dimethylamino)ethyl 3-fluoro-5-(2-(3-(6-methylpyridin-2-yl)-4-(quinolin-4-yl)-1H-pyrazol-1-yl)acetamido)benzoate | A |
| 4 | 2-morpholinoethyl 3-fluoro-5-(2-(3-(6-methylpyridin-2-yl)-4-(quinolin-4-yl)-1H-pyrazol-1-yl)acetamido)benzoate | A |
| 5 | 2-(dimethylamino)ethyl 5-(2-(3-(6-methylpyridin-2-yl)-4-(quinolin-4-yl)-1H-pyrazol-1-yl)acetamido)picolinate | B |
| 6 | 2-(4-methylpiperazin-1-yl)ethyl 3-fluoro-5-(2-(3-(6-methylpyridin-2-yl)-4-(quinolin-4-yl)-1H-pyrazol-1-yl)acetamido)benzoate | A |
| 7 | 2-(diethylamino)ethyl 3-fluoro-5-(2-(3-(6-methylpyridin-2-yl)-4-(quinolin-4-yl)-1H-pyrazol-1-yl)acetamido)benzoate | A |
| 9 | (1-methylpiperidin-4-yl)methyl 3-fluoro-5-(2-(3-(6-methylpyridin-2-yl)-4-(quinolin-4-yl)-1H-pyrazol-1-yl)acetamido)benzoate | A |
| 15 | 2-(methylamino)ethyl 3-fluoro-5-(2-(3-(6-methylpyridin-2-yl)-4-(quinolin-4-yl)-1H-pyrazol-1-yl)acetamido)benzoate | B |
| 19 | 2-(piperazin-1-yl)ethyl 3-fluoro-5-(2-(3-(6-methylpyridin-2-yl)-4-(quinolin-4-yl)-1H-pyrazol-1-yl)acetamido)benzoate | A |
| 21 | piperidin-4-yl 3-fluoro-5-(2-(3-(6-methylpyridin-2-yl)-4-(quinolin-4-yl)-1H-pyrazol-1-yl)acetamido)benzoate | B |

Ranges:
A: $IC_{50}$ =< 1 μM
B: $IC_{50}$ > 1 μM

As can be seen from the results described in Table 2, the compounds of the present invention are potent inhibitors of transforming growth factor-β receptor I ((TGFβRI)/ALK5).

Determination of Plasma Stability of Some Compounds

Human plasma pooled from healthy donors extracted in citrate tubes was employed in the assay. Briefly, plates containing 10 μM compounds in plasma (total volume: 50

μL) were incubated at 37° C. at the different times (0, 30, 120 and 360 min). Then 100 μl Acetonitrile were added for precipitating plasma protein, and the plate was centrifuged at 46000 g for 60 min at 5° C. Supernatant was taken and analysed by UPLC/MS/MS for sample quantification. Stationary phase: Reverse phase Acquity UPLC® BEH C18 1.7 μm (2.1 mm×50 mm) (Waters). Mobile phase: 0.1% Formic acid water/0.1% formic acid in acetonitrile.
Gradient:

| Time (min) | Water | Acetonitrile |
|---|---|---|
| 0 | 95% | 5% |
| 0.1 | 95% | 5% |
| 1 | 0% | 100% |
| 2 | 0% | 100% |
| 2.2 | 95% | 5% |
| 2.5 | 95% | 5% |

Flow: 0.6 ml/min. The chromatographic equipment employed was an UPL QSM Waters Acquity. Compound concentrations were calculated from the MS peak areas.
Results Table 3 shows the results of assays described below of some compounds. It shows remaining percentage for each of the studied compounds at human plasma at the different times tested.

TABLE 3

| Example | 0 min (%) | 30 min (%) | 120 min (%) | 360 min (%) |
|---|---|---|---|---|
| 1 | 100 | 0 | 0 | 0 |
| 5 | 100 | 10 | 0 | 0 |
| 7 | 100 | 16.0 | 3.3 | 0.1 |
| 9 | 100 | 16.6 | 3.1 | 0 |
| 18 | 100 | 33.9 | 11.1 | 0.1 |
| 19 | 100 | 1.9 | 0.3 | 0 |
| 21 | 100 | 74.3 | 34.2 | 6.3 |
| Comparative example 1 | 100 | 100 | 88 | 87 |
| Comparative example 2 | 100 | 83 | 69 | 67 |
| Comparative example 3 | 100 | 99 | 96 | 73 |

All the studied examples of the present invention showed low stability in human plasma, unlike compounds of comparative example 1, comparative example 2 and comparative example 3 which were remaining up to 60% of initial amount after 6 hours.

The derivatives of the invention are useful in the treatment or prevention of diseases known to be susceptible to improvement by treatment with an inhibitor of transforming growth factor-β receptor I (TGFβRI)/ALK5. Such diseases are respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

Accordingly, the derivatives of the invention and pharmaceutically acceptable salts thereof, and pharmaceutical compositions comprising such compounds and/or salts thereof, may be used in a method of treatment of disorders of the human body which comprises administering to a subject requiring such treatment an effective amount of ester derivatives of the present invention or a pharmaceutically acceptable salt thereof.

The present invention also provides pharmaceutical compositions which comprise, as an active ingredient, at least an ester derivatives of formula (I) or a pharmaceutically acceptable salt thereof in association with, other therapeutics agents a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application.

Preferably, compounds of formula (I), pharmaceutically acceptable salts and compositions thereof are made up in a form suitable for inhale, nasal, oral, topical, or ocular administration. In a more preferably way, compounds of formula (I), pharmaceutically acceptable salts and compositions thereof are made up in a form suitable for inhale administration.

The pharmaceutically acceptable excipients, which are admixed with the active compound or salts of such compound, to form the compositions of this invention, are well known per se and the actual excipients used depend inter alia on the intended method of administering the compositions.

Compounds of formula (I), pharmaceutically acceptable salts thereof and compositions of this invention are preferably adapted for per os administration. In this case, the compositions for oral administration may take the form of inhalation aerosols, inhalation solutions, dry powder inhalation, tablets, retard tablets, sublingual tablets, capsules, or liquid preparations, such as mixtures, elixirs, syrups or suspensions, all containing the compound of the invention; such preparations may be made by methods well-known in the art.

The administration of compound of formula (I) to a mammal in the treatment of a respiratory diseases such as pulmonary fibrosis, asthma, chronic obstructive pulmonary disease, adult respiratory distress syndrome, interstitial pulmonary fibrosis, pulmonary arterial hypertension and lung cancer; fibrotic skin diseases, such as scleroderma, nephrogenic fibrosing dermopathy, mixed connective tissue disease, scleromyxedema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy are a particular aspect of the present invention may be carried out in any feasible way. Preferably the administration is oral. Preferably, oral administration is inhaled administration.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in any way.

The synthesis of the compounds of the invention is illustrated by the following examples including the preparation of the intermediates, which do not limit the scope of the invention in any way.

EXAMPLES

General. Reagents, solvents and starting products were acquired from commercial sources. The term "concentration" refers to the vacuum evaporation using a Buchi rotavapor. When indicated, the reaction products were purified by "flash" chromatography on silica gel (40-63 μm) with the indicated solvent system or using a Vertex CombiFlash system. The spectroscopic data were measured in a Varian Mercury 300 spectrometer. The melting points were measured in a BQchi 535 instrument. The HPLC-MS were performed on a Gilson instrument equipped with a Gilson 321 piston pump, a Gilson 864 vacuum degasser, a Gilson 189 injection module, a 1/1000 Gilson splitter, a Gilson 307 pump, a Gilson 170 detector, and a Thermoquest Fennigan aQa detector. The UPLC-MS were performed on an Acquity H-Class (Waters) equipped with an Acquity sample manager, an Acquity quaternary solvent manager, an Acquity PDA detector, an Acquity QDA detector and a Vaccubrand vacuum pump

Intermediate 1: 1-(6-methylpyridin-2-yl)-2-(quinolin-4-yl)ethan-1-one

To a solution of 4-methylquinoline (5.0 g, 34.91 mmol) in THF (50 mL) and cooled at −30° C. with the aid of an external $CO_2$/acetone bath, LiHMDS (105 mL, 104.73 mmol) was dropwise added for 1 h and the reaction mixture was stirred at low temperature for 1 h. The reaction was cooled at −30° C. and ethyl 6-methylpyridine-2-carboxylate (6.3 g, 41.90 mmol) was dropwise added for 5 min and the mixture was stirred for 18 h allowed to reach room temperature. The suspension resulting was filtered, washing with THF (40 mL) to give a yellow solid (7.04 g, 76%).

$^1$H-NMR (300 MHz, $CDCl_3$): δ=8.84 (d, J=4.4 Hz, 1H), 8.138-8.045 (m, 2H), 7.85 (d, J=7.6 Hz, 1H), 7.74-7.66 (m, 2H), 7.56-7.51 (m, 1H), 7.41 (d, J=4.4 Hz, 1H), 7.36 (dd, J=7.6, 0.5 Hz, 1H), 5.02 (s, 2H), 2.67 (s, 3H).

HPLC-MS: Rt 10.077 m/z 262.7 $[M+H]^+$.

Intermediate 2: 4-(3-(6-methylpyridin-2-yl)-1H-pyrazol-4-yl)quinoline

To a solution of 1-(6-methylpyridin-2-yl)-2-(quinolin-4-yl)ethan-1-one (7.04 g, 26.58 mmol) in DMF (35 mL) cooled with the aid of an external ice/$H_2O$ bath at 9° C. DMF-DMA (10.6 mL, 79.75 mmol) was added for 8 min. AcOH (5.5 mL, 95.68 mmol) was added dropwise and the reaction mixture was stirred for 17 h allowed to reach room temperature. The reaction mixture was cooled at 7° C. with an external ice/$H_2O$ bath and $N_2H_4H_2O$ (6.45 mL, 50.06 mmol, 64-65%) was added dropwise and stirred at low temperature for 3 h. $H_2O$ (70 mL) was added dropwise and the suspension resulting was stirred at room temperature overnight. The suspension resulting was filtered and washed with $H_2O$ (60 mL) to give a beige solid (3.45 g, 45%).

$^1$H-NMR (300 MHz, DMSO-$d_6$): δ=13.63 (br s, 1H), 8.81 (br s, 1H), 8.04 (d, J=9.6 Hz, 1H), 7.73-7.40 (m, 7H), 7.02 (m, 1H), 2.50 (s, 3H).

HPLC-MS: Rt 9.100 m/z 286.9 $[M+H]^+$.

Intermediate 3: tert-butyl 2-hydroxyethylisopropylcarbamate

To a solution of 2-(isopropylamino)ethanol (1.4 g, 9.69 mmol) in dichloromethane (10 mL), cooled down to 5° C. with the aid of an external ice/water bath, a solution of tert-butyl dicarbonate (2.5 g, 11.63 mmol) in dichloromethane (5 mL) was added. The reaction mixture was allowed to reach room temperature and stirred for 22 h, diluted with dichloromethane (10 mL), washed with ammonium chloride (2×15 mL, aqueous saturated solution) and with citric acid (15 mL, aqueous solution 1 M). The organic layer was dried over sodium sulfate and concentrated to give a yellow oil (2.1 g). The product was used in the next step without additional purification.

$^1$H NMR (300 MHz, $CDCl_3$) δ=4.17 (s, 1H), 3.69 (t, J=5.6 Hz, 2H), 3.30-3.25 (m, 2H), 1.46 (s, 9H), 1.11 (dd, J=6.8, 1.2 Hz, 6H).

The following intermediates, from 4 to 10, were prepared following the procedure describe for Intermediate 3.

Intermediate 4: tert-butyl 2-hydroxyethylcarbamate $^1$H NMR (300 MHz, $CDCl_3$) δ=3.71 (t, J=5.0 Hz, 2H), 3.30 (t, J=5.0 Hz, 2H), 1.46 (s, 9H).

Intermediate 5: tert-butyl 2-hydroxyethylmethylcarbamate $^1$H NMR (300 MHz, $CDCl_3$) δ 3.76 (t, J=5.3 Hz, 2H), 3.41 (t, J=5.3 Hz, 2H), 2.93 (s, 3H), 1.48 (s, 9H).

Intermediate 6: tert-butyl ethyl 2-hydroxyethylcarbamate $^1$H NMR (300 MHz, $CDCl_3$) δ=3.72 (t, J=5.2 Hz, 2H), 3.35 (t, J=5.2 Hz, 2H), 3.26 (q, J=7.0 Hz, 2H), 2.58 (s, 1H), 1.46 (s, 9H), 1.10 (t, J=7.0 Hz, 3H).

Intermediate 7: tert-butyl 4-(2-hydroxyethyl)piperazine-1-carboxylate $^1$H NMR (300 MHz, $CDCl_3$) δ=3.62 (t, J=5.4 Hz, 2H), 3.43 (t, J=5.1 Hz, 4H), 2.55 (t, J=5.4 Hz, 2H), 2.45 (t, J=5.1 Hz, 4H), 1.44 (s, 9H).

Intermediate 8: tert-butyl 4-(hydroxymethyl)piperidine-1-carboxylate $^1$H NMR (300 MHz, $CDCl_3$) δ=4.12 (d, J=13.4 Hz, 2H), 3.56-3.42 (m, 2H), 2.70 (t, J=12.9 Hz, 2H), 1.71 (d, J=13.9 Hz, 2H), 1.60-1.45 (m, 11H), 1.19-1.08 (m, 1H).

Intermediate 9: tert-butyl 4-hydroxypiperidine-1-carboxylate $^1$H NMR (300 MHz, $CDCl_3$) δ=4.00-3.70 (m, 3H), 3.02 (ddd, J=13.4, 9.8, 3.3 Hz, 2H), 1.63 (sa, 2H), 1.95-1.77 (m, 2H), 1.45 (s, 9H).

Intermediate 10: tert-butyl 6-bromopyridine-3-carboxylate

To a suspension of 6-bromopyridine-3-carboxylic acid (1 g, 4.95 mmol) and (4-dimethylamino)pyridine (50 mg, 0.08 mmol) in THF (15 mL) a solution of di-tert-butyl dicarbonate (2.7 g, 12.38 mmol) in THF (2 mL) was added dropwise and the reaction mixture was refluxed for 5 h. The reaction was allowed to reach room temperature and was stirred for 17 h. The solvent was evaporated under reduced pressured and the residue was dissolved in MTBE (10 mL) and washed with $H_2O$ (×10 mL), with citric acid (10 ml, aqueous solution 0.5 M), with $H_2O$ (10 mL) and with $NaHCO_3$ (10 mL, aqueous saturated solution). The organic layer was dried over sodium sulfate and concentrated to dryness to afford an yellow solid (0.890 g, 70%). The product was used in the next step without additional purification.

HPLC-MS: Rt 3.791 m/z 258.1 $[M+H]^+$.

Intermediate 11: tert-butyl 5-aminopicolinate

Cuprous iodide (0.510 g, 2.68 mmol), trans-4-hydroxy-L-proline (0.703 g, 5.36 mmol) and tert-butyl 5-bromopicolinate (3.46 g, 13.40 mmol) were stirred with dimethylsulfoxide (20 mL) in a sealed tube. Concentrated ammonium hydroxide (15 mL) was added and the tube was closed and the homogeneous blue solution was heated at 80° C. for 17 hours. The reaction mixture was allowed to reach room temperature and filtered. The resulting solid was dissolved in dichloromethane (30 mL) and washed with saturated ammonium chloride solution (50 mL). The aqueous layers were extracted with dichloromethane (2×30 mL) and the combined organic extracts were dried over sodium sulfate and concentrated to afford a white solid (2.16 g, 83%).

$^1$H-NMR (300 MHz, $CDCl_3$): δ=8.13 (br. s, 1H), 7.86 (d, J=8.8 Hz, 1H), 6.95 (dd, J=8.8, 2.3 Hz, 1H), 1.61 (s, 9H).

HPLC-MS: Rt 8.607 m/z 195.2 $[M+H]^+$.

The following intermediate 12 was prepared following the procedure describe for Intermediate 11.

Intermediate 12: tert-butyl 6-aminopyridine-3-carboxylate

HPLC-MS: Rt 3.262 m/z 195.3 $[M+H]^+$.

Intermediate 13: tert-butyl 5-(2-bromoacetamido)picolinate tert-Butyl 5-aminopicolinate (1.07 g, 5.51 mmol) was suspended in dichloromethane (15 mL) and cooled to 0° C. Triethylamine (0.84 mL, 6.06 mmol) was added followed by addition dropwise of a solution of bromoacetyl bromide (0.67 mL, 7.71 mmol) in dichloromethane (2 mL). The reaction mixture was stirred at 0° C. for 40 min. and then allowed to warm to room temperature. The resulting suspension was filtered, washing with dichloromethane (5 mL). The solid was purified by flash chromatography on silice gel (2→3% MeOH/$CH_2Cl_2$) to give an orange solid (1.11 g, 64%).

$^1$H-NMR (300 MHz, DMSO-$d_6$): δ=10.97 (s, 1H), 8.79 (d, J=2.6 Hz, 1H), 8.24 (dd, J=8.5, 2.6 Hz, 1H), 8.01 (d, J=8.5 Hz, 1H), 4.11 (s, 2H), 1.54 (s, 9H).

HPLC-MS: Rt 9.514 m/z 313.0-315.0 $[M-H]^-$.

Intermediate 14: 3-(2-bromoacetamido)-5-fluorobenzoic acid

To a solution of 3-amino-5-fluorobenzoic acid (6.0 g, 38.67 mmol) in THF (60 mL), cooled in an external $H_2O$/ice bath, 2-bromoacetyl bromide (3.7 mL, 42.54 mmol) was added and the reaction mixture was stirred at low temperature for 10 min, allowed to reach room temperature and stirred for 22 h. The suspension resulting was filtered, washing with EtOAc (30 mL) and the mother liquor was concentrated to dryness and the solid was slurried with a mixture of $Et_2O$:hexanes 1:1 (25 mL) to furnish a white solid (7.4 g, 70%).

$^1$H NMR (300 MHz, DMSO-$d_6$) δ 10.79 (s, 1H), 7.95 (t, J=1.4 Hz, 1H), 7.79 (dt, J=10.9, 2.2 Hz, 1H), 7.38 (ddd, J=8.9, 2.2, 1.4 Hz, 1H), 4.06 (s, 2H).

HPLC-MS: Rt 1.89 m/z 276.2 $[M+H]^+$.

The following intermediates, from 15 to 16, were prepared following the procedure describe for Intermediate 14.

Intermediate 15: tert-butyl 6-(2-bromoacetamido)pyridine-3-carboxylate $^1$H NMR (60 MHz, DMSO-$d_6$) b 8.80 (dd, J=2.1, 1.1 Hz, 1H), 8.19 (t, J=1.8 Hz, 2H), 4.17 (s, 2H), 1.55 (s, 9H).

HPLC-MS: Rt 3.658 m/z 317.1 $[M+H]^+$.

Intermediate 16: 5-(2-bromoacetamido)pyridine-3-carboxylic acid $^1$H NMR (60 MHz, DMSO-$d_6$) δ 10.98 (s, 1H), 9.17-8.49 (m, 2H), 8.57-7.81 (m, 1H), 4.08 (s, 2H).

HPLC-MS: Rt 1.205 m/z 257.1-259.2 $[M+H]^+$.

Intermediate 17: 3-(2-(3-(6-methylpyridin-2-yl)-4-(quinolin-4-yl)-1H-pyrazol-1-yl)acetamido)-5-fluorobenzoic acid To a suspension of 4-(3-(6-methylpyridin-2-yl)-1H-pyrazol-4-yl)quinoline (3.5 g, 12.26 mmol) in THF (100 mL) cooled at −11° C. with the aid of an external EtOH/ice bath NaH (1.5 g, 36.78 mmol. 60% dispersion in mineral oil) was added in one portion and the reaction mixture was stirred at low temperature for 30 min. A solution of 3-(2-bromoacetamido)-5-fluorobenzoic acid (4.4 g, 15.94 mmol) in THF (100 mL) was added dropwise for 45 min and the mixture was stirred for 3 h, allowed to reach room temperature overnight. Silice was added and the solvent was concentrated in vacuo.

The residue was purified by flash chromatography on silice gel (8→15% MeOH/$CH_2Cl_2$+1% AcOH) to give a beige solid (4.71 g, 80%).

$^1$H NMR (300 MHz, DMSO-$d_6$) δ=10.90 (s, 1H), 8.88 (d, J=4.5 Hz, 1H), 8.18 (s, 1H), 8.10-7.96 (m, 2H), 7.85-7.69 (m, 3H), 7.64-7.31 (m, 5H), 6.98 (d, J=7.5 Hz, 1H), 5.27 (s, 2H), 1.82 (s, 3H).

HPLC-MS: Rt 3.018 m/z 482.1 $[M+H]^+$.

The following intermediates, from 18 to 19, were prepared following the procedure describe for Intermediate 17.

Intermediate 18: tert-butyl 5-(2-(3-(6-methylpyridin-2-yl)-4-(quinolin-4-yl)-1H-pyrazol-1-yl)acetamido)picolinate The residue was purified by flash chromatography on silice gel (2.5→4% MeOH/$CH_2Cl_2$) to give a yellow solid (0.950 g, 69%).

$^1$H-NMR (300 MHz, $CDCl_3$): δ=10.83 (s, 1H), 8.92 (dd, J=4.7, 1.4 Hz, 1H), 8.54 (m, 1H), 8.30-8.26 (m, 1H), 8.18 (d, J=8.5 Hz, 1H), 7.95 (d, J=8.2 Hz, 1H), 7.80-7.69 (m, 3H), 7.49-7.31 (m, 3H), 7.00 (d, J=7.9 Hz, 1H), 6.90 (d, J=7.9 Hz, 1H), 5.29 (s, 2H), 2.37 (s, 3H), 1.62 (s, 9H).

HPLC-MS: Rt 10.376 m/z 521.1 $[M+H]^+$.

Intermediate 19: tert-butyl 6-(2-(3-(6-methylpyridin-2-yl)-4-(quinolin-4-yl)-1H-pyrazol-1-yl)acetamido)pyridine-3-carboxylate $^1$H NMR (300 MHz, DMSO-$d_6$) δ 11.20 (s, 1H), 8.68 (m, 1H), 8.26-7.64 (m, 4H), 7.72-7.02 (m, 7H), 6.81 (d, J=7.4 Hz, 1H), 5.19 (s, 2H), 1.67 (s, 3H), 1.39 (s, 9H).

HPLC-MS: Rt 4.011 m/z 521.3-522.2 $[M+H]^+$.

Intermediate 20: 5-(2-(3-(6-methylpyridin-2-yl)-4-(quinolin-4-yl)-1H-pyrazol-1-yl)acetamido)picolinic acid A solution of tert-butyl 5-(2-(3-(6-methylpyridin-2-yl)-4-(quinolin-4-yl)-1H-pyrazol-1-yl)acetamido)picolinate (0.170 mg, 0.518 mmol) in a hydrochloric acid solution (8 ml, solution 4M in dioxane) was refluxed for 2 h and allowed to reach room temperature. EtOAc (2×15 mL) was added and the solvents were removed in vacuo. The residue crude was purified by C18 chromatography with a Combiflash system (5→100% $H_2O$/MeCN) to give a beige solid (0.063 g, 26%).

$^1$H-NMR (300 MHz, DMSO-$d_6$): δ=11.06 (s, 1H), 8.91 (s, 1H), 8.85 (d, J=4.4 Hz, 1H), 8.26 (d, J=8.1 Hz, 1H), 8.18 (s, 1H), 8.05 (t, J=9.3 Hz, 2H), 7.72-7.37 (m, 6H), 6.98 (d, J=7.5 Hz, 1H), 5.33 (s, 2H), 1.83 (s, 3H).

HPLC-MS: Rt 12.726 m/z 465.0 $[M+H]^+$.

The following intermediate 21 was prepared following the procedure describe for Intermediate 20.

Intermediate 21: 6-(2-(3-(6-methylpyridin-2-yl)-4-(quinolin-4-yl)-1H-pyrazol-1-yl)acetamido)pyridine-3-carboxylic acid HPLC-MS: Rt 3.158 m/z 465.1 $[M+H]^+$.

Intermediate 22: tert-butyl 2-(3-(2-(3-(6-methylpyridin-2-yl)-4-(quinolin-4-yl)-1H-pyrazol-1-yl)acetamido)-5-fluorobenzoyloxy)ethylethylcarbamate To a suspension of 3-(2-(3-(6-methylpyridin-2-yl)-4-(quinolin-4-yl)-1H-pyrazol-1-yl)acetamido)-5-fluorobenzoic acid (0.20 g, 0.415 mmol) in DMF (4 mL) N,N-diisopropylethylamine (0.21 mL, 1.24 mmol) and 1-[bis(dimethylamino)methylene]-1H-1,2,3-triazolo[4,5-b]pyridinium 3-oxide hexafluorophosphate (0.26 g, 0.622 mmol) were added and the reaction mixture was stirred at room temperature for 30 min. A solution of tert-butyl ethyl2-hydroxyethylcarbamate (0.15 g, 0.830 mmol) in DMF (1 mL) was added and the mixture was stirred at room temperature for 2 h. The reaction mixture was diluted with EtOAc (15 mL) and washed with brine (3×10 mL). The organic layer was dried over sodium sulfate and concentrated to give a brown oil (0.3 g) that was used in the next step without additional purification.

HPLC-MS: Rt 4.021 m/z 653.3 $[M+H]^+$.

The following intermediates, from 23 to 28, were prepared following the procedure describe for Intermediate 22

Intermediate 23: tert-butyl 2-(3-(2-(3-(6-methylpyridin-2-yl)-4-(quinolin-4-yl)-1H-pyrazol-1-yl)acetamido)-5-fluorobenzoyloxy)ethylisopropylcarbamate HPLC-MS: Rt 4.112 m/z 667.3 $[M+H]^+$.

Intermediate 24: tert-butyl 2-(3-(2-(3-(6-methylpyridin-2-yl)-4-(quinolin-4-yl)-1H-pyrazol-1-yl)acetamido)-5-fluorobenzoyloxy)ethylcarbamate HPLC-MS: Rt 3.878 m/z 625.3 $[M+H]^+$.

Intermediate 25: tert-butyl 2-(3-(2-(3-(6-methylpyridin-2-yl)-4-(quinolin-4-yl)-1H-pyrazol-1-yl)acetamido)-5-fluorobenzoyloxy)ethylmethylcarbamate HPLC-MS: Rt 3.954 m/z 639.3 $[M+H]^+$.

Intermediate 26: tert-butyl 4-(2-(3-(2-(3-(6-methylpyridin-2-yl)-4-(quinolin-4-yl)-1H-pyrazol-1-yl)acetamido)-5-fluorobenzoyloxy)ethyl)piperazine-1-carboxylate HPLC-MS: Rt 3.981 m/z 694.2 $[M+H]^+$.

Intermediate 27: tert-butyl 4-((3-(2-(3-(6-methylpyridin-2-yl)-4-(quinolin-4-yl)-1H-pyrazol-1-yl)acetamido)-5-fluorobenzoyloxy)methyl)piperidine-1-carboxylate HPLC-MS: Rt 4.091 m/z 679.3 $[M+H]^+$.

Intermediate 28: tert-butyl 4-(3-(2-(3-(6-methylpyridin-2-yl)-4-(quinolin-4-yl)-1H-pyrazol-1-yl)acetamido)-5-fluorobenzoyloxy)piperidine-1-carboxylate HPLC-MS: Rt 4.060 m/z 665.3 $[M+H]^+$.

Intermediate 29: methyl 3-(2-bromoacetamido)-5-chlorobenzoate

HPLC-MS: Rt 9.991 m/z 306.0 $[M-H]^-$.

This intermediate was prepared following the procedure describe for intermediate 17.

Examples

Example 1: 2-(dimethylamino)ethyl 3-fluoro-5-(2-(3-(6-methylpyridin-2-yl)-4-(quinolin-4-yl)-1H-pyrazol-1-yl)acetamido)benzoate To a suspension of 3-(2-(3-(6-methylpyridin-2-yl)-4-(quinolin-4-yl)-1H-pyrazol-1-yl)acetamido)-5-fluorobenzoic acid (2.0 g, 4.150 mmol) in dichloromethane (50 mL) thionyl chloride (1.5 mL, 20.75 mmol) was added and the reaction mixture was heated under refluxed overnight. The reaction was allowed to reach room temperature and the solvent was evaporated under reduced pressured. The residue was suspended in dichloromethane (50 mL) and 2-(dimethylamino)ethanol (0.59 mL, 6.22 mmol) and N,N-diisopropylethylamine (3 mL, 17.48 mmol) were added and the mixture was stirred at room temperature for 30 min. The reaction mixture was poured on water (50 mL), the phases were separated and the organic phase was washed with water (50 mL) and with brine (50 mL). To organic layer an aqueous citric acid solution was added to reach pH 1.7, the layers were separated and the final organic layer was dried over sodium sulfate and concentrated to dryness. Acetonitrile (25 mL) was added to the residue and the mixture was stirred at room temperature for 20 min, heated to 55° C. for 15 min and allowed to reach room temperature overnight. The resulting suspension was filtered, washing with acetonitrile (15 mL) to give a beige solid (1.24 g, 54%).

$^1$H NMR (300 MHz, DMSO-$d_6$) δ=10.95 (s, 1H), 8.84 (d, J=4.4 Hz, 1H), 8.32-7.10 (m, 11H), 6.96 (d, J=7.4 Hz, 1H), 5.22 (s, 2H), 4.36 (t, J=5.6 Hz, 2H), 2.60 (t, J=5.6 Hz, 2H), 2.19 (s, 6H), 1.82 (s, 3H).

UPLC-MS: Rt 3.562 m/z 553.4-554.4 $[M+H]^+$.

The following examples, from 2 to 3, were prepared following the procedure described for the Example 1.

Example 2: 2-(dimethylamino)ethyl 5-(2-(3-(6-methylpyridin-2-yl)-4-(quinolin-4-yl)-1H-pyrazol-1-yl)acetamido)nicotinate $^1$H NMR (300 MHz, DMSO-$d_6$) δ 10.99 (s, 1H), 9.01 (d, J=2.5 Hz, 1H), 8.84 (dd, J=10.2, 3.2 Hz, 2H), 8.65 (t, J=2.2 Hz, 1H), 8.19 (s, 1H), 8.04 (d, J=8.3 Hz, 1H), 7.81-7.27 (m, 7H), 6.98 (d, J=7.4 Hz, 1H), 5.32 (s, 2H), 4.40 (t, J=5.7 Hz, 2H), 2.63 (t, J=5.7 Hz, 2H), 2.21 (s, 6H), 1.84 (s, 3H).

UPLC-MS: Rt 2.853 m/z 536.4-537.4 $[M+H]^+$.

Example 3: 2-(dimethylamino)ethyl 6-(2-(3-(6-methylpyridin-2-yl)-4-(quinolin-4-yl)-1H-pyrazol-1-yl)acetamido)nicotinate $^1$H NMR (300 MHz, DMSO-$d_6$) δ 11.43 (s, 1H), 9.07-8.66 (m, 2H), 8.46-7.88 (m, 4H), 7.81-7.23 (m, 6H), 6.98 (d, J=7.4 Hz, 1H), 5.37 (s, 2H), 4.37 (t, J=5.7 Hz, 2H), 2.62 (t, J=5.7 Hz, 2H), 2.22 (s, 6H), 1.84 (s, 3H).

UPLC-MS: Rt 2.911 m/z 536.4-537.4 $[M+H]^+$.

Example 4: 2-morpholinoethyl 3-fluoro-5-(2-(3-(6-methylpyridin-2-yl)-4-(quinolin-4-yl)-1H-pyrazol-1-yl)acetamido)benzoate To a suspension of 3-(2-(3-(6-methylpyridin-2-yl)-4-(quinolin-4-yl)-1H-pyrazol-1-yl)acetamido)-5-fluorobenzoic acid (0.200 g, 0.397 mmol) in dichloromethane (8 mL) thionyl chloride (0.290 mL, 3.97 mmol) was added and the reaction mixture was heated under refluxed 3 h, allowed to reach room temperature and the solvent was evaporated under reduced pressured. The residue was suspended in dichloromethane (8 mL) and 2-morpholinoethanol (0.145 mL, 1.19 mmol) was added, stirring the mixture at room temperature overnight. The solvent was removed in vacuo, the residue was dissolved in EtOAc (20 mL) and washed with sodium bicarbonate (2×20 mL, aqueous saturated solution). The organic phase was dried over sodium sulfate and concentrated. The reaction product was suspended in MeCN (10 mL), stirred at room temperature for 4 h and the resulting suspension was filtered, washing with MeCN (2×5 mL) to afford a white solid (0.130 g, 55%).

$^1$H NMR (300 MHz, DMSO-$d_6$) δ=10.93 (s, 1H), 8.83 (d, J=4.5 Hz, 1H), 8.15 (s, 1H), 8.02 (d, J=8.0 Hz, 2H), 7.85 (d, J=11.1 Hz, 1H), 7.74-7.25 (m, 7H), 6.96 (d, J=7.5 Hz, 1H), 5.25 (s, 2H), 4.39 (t, J=5.8 Hz, 2H), 3.53 (t, J=4.6 Hz, 4H), 2.67 (t, J=5.8 Hz, 2H), 2.44 (m, 4H), 1.81 (s, 3H).

UPLC-MS: Rt 3.449 m/z 595.4-596.4 $[M+H]^+$.

The following examples, from 5 to 8, were synthesized using the procedure described for the Example 4.

Example 5: 2-(dimethylamino)ethyl 5-(2-(3-(6-methylpyridin-2-yl)-4-(quinolin-4-yl)-1H-pyrazol-1-yl)acetamido)picolinate $^1$H NMR (300 MHz, DMSO-$d_6$) δ=11.07 (s, 1H), 8.93-8.81 (m, 2H), 8.30 (d, J=8.8 Hz, 1H), 8.17 (s, 1H), 8.06 (dd, J=13.5, 8.4 Hz, 2H), 7.76-7.34 (m, 6H), 6.98 (d, J=7.7 Hz, 1H), 5.33 (s, 2H), 4.37 (t, J=6.1 Hz, 2H), 2.61 (t, J=6.1 Hz, 2H), 2.21 (s, 6H), 1.84 (s, 3H).

UPLC-MS: Rt 2.682 m/z 536.5 $[M+H]^+$.

Example 6: 2-(4-methylpiperazin-1-yl)ethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=10.94 (s, 1H), 8.83 (d, J=4.4 Hz, 1H), 8.29-7.23 (m, 11H), 6.96 (d, J=7.6 Hz, 1H), 5.26 (s, 2H), 4.36 (br s, 2H), 2.66 (br s, 2H), 2.48 (br s, 4H), 2.27 (br s, 4H), 2.09 (s, 3H), 1.82 (s, 3H).

UPLC-MS: Rt 3.083 m/z 608.3-609.3 $[M+H]^+$.

Example 7: 2-(diethylamino)ethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=10.94 (s, 1H), 8.84 (d, J=4.4 Hz, 1H), 8.25-7.23 (m, 11H), 6.96 (d, J=7.5 Hz, 1H), 5.26 (s, 2H), 4.34 (t, J=5.8 Hz, 2H), 2.82 (t, J=5.8 Hz, 2H), 2.59 (q, J=7.1 Hz, 4H), 1.82 (s, 3H), 0.97 (t, J=7.1 Hz, 6H).

UPLC-MS: Rt 3.393 m/z 581.4-582.4 $[M+H]^+$.

Example 8: 1-methylpiperidin-4-yl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=10.93 (s, 1H), 8.84 (d, J=4.5 Hz, 1H), 8.29-7.76 (m, 5H), 7.79-7.24 (m, 7H), 6.96 (d, J=7.5 Hz, 1H), 5.26 (s, 2H), 4.97 (br s, 1H), 2.70 (br s, 2H), 2.28 (br s, 2H), 1.94 (br s, 2H), 1.82 (m, 5H).

UPLC-MS: Rt 3.248 m/z 579.4-580.4 $[M+H]^+$.

Example 9: (1-methylpiperidin-4-yl)methyl 3-fluoro-5-(2-(3-(6-methylpyridin-2-yl)-4-(quinolin-4-yl)-1H-pyrazol-1-yl)acetamido)benzoate To a solution of 3-(2-(3-(6-methylpyridin-2-yl)-4-(quinolin-4-yl)-1H-pyrazol-1-yl)acetamido)-5-fluorobenzoic acid (0.20 g, 0.415 mmol) in N,N-dimethylformamide (4 mL) N,N-diisopropylethylamine (0.21 mL, 1.24 mmol), hydroxybenzotriazole (0.125 g, 0.623 mmol) and 1-ethyl-3-(3-dimethylaminopropyl)carbodiimide (0.120 g, 0.623 mmol) were added and the reaction mixture was stirred at room temperature for 40 min. A solution of (1-methylpiperidin-4-yl)methanol (0.11 g, 0.830 mmol) in N,N-dimethylformamide (1 mL) was added continuing to stir the mixture at room temperature for 3 h. The reaction mixture was diluted with EtOAc (20 mL) and washed with brine (3×15 mL). The organic layer was dried over sodium sulfate and concentrated under reduced pressure. The residue was purified by C18 chromatography with a Combiflash system (5→80% $H_2O$/MeCN+0.1% formic acid) to afford a white-off solid (0.015 g, 6%). 20 $^1$H NMR (300 MHz, DMSO-$d_6$) δ=11.02 (s, 1H), 8.86 (d, J=4.5 Hz, 1H), 8.24-7.84 (m, 5H), 7.78-7.28 (m, 6H), 6.98 (d, J=7.5 Hz, 1H), 5.28 (s, 2H), 4.18 (d, J=5.8 Hz, 2H), 2.88 (d, J=11.2 Hz, 2H), 2.24 (s, 3H), 2.04

(t, J=11.2 Hz, 2H), 1.84 (s, 3H), 1.73 (d, J=11.9 Hz, 3H), 1.39 (t, J=11.9 Hz, 2H).

UPLC-MS: Rt 3.141 m/z 593.4-594.4 $[M+H]^+$.

Example 10: (R)-quinuclidin-3-yl 3-fluoro-5-(2-(3-(6-methylpyridin-2-yl)-4-(quinolin-4-yl)-1H-pyrazol-1-yl)acetamido)benzoate To a suspension of 3-(2-(3-(6-methylpyridin-2-yl)-4-(quinolin-4-yl)-1H-pyrazol-1-yl)acetamido)-5-fluorobenzoic acid (0.20 g, 0.415 mmol) in N,N-dimethylformamide (4 mL) N,N-diisopropiletilamina (0.21 mL, 1.24 mmol) and 1-[bis(dimethylamino)methylene]-1H-1,2,3-triazolo[4,5-b]pyridinium 3-oxide hexafluorophosphate (0.23 g, 0.623 mmol) were added and the reaction mixture was stirred at room temperature for 30 min. To the reaction mixture (R)-quinuclidin-3-ol (0.105 g, 0.830 mmol) was added continuing with stirring at room temperature overnight. The reaction mixture was diluted with EtOAc (30 mL) and washed with brine (2×20 mL). The organic layer was dried over sodium sulfate and concentrated under reduced pressure. The residue was purified by C18 chromatography with a Combiflash system (5→80% $H_2O$/MeCN+0.1% formic acid) to afford a white-off solid (0.057 g, 23%).

$^1$H NMR (400 MHz, DMSO-$d_6$) δ=10.95 (s, 1H), 8.83 (d, J=4.4 Hz, 1H), 8.16 (d, J=11.7 Hz, 2H), 8.02 (tt, J=3.7, 1.0 Hz, 2H), 7.91 (dt, J=10.9, 2.3 Hz, 1H), 7.77-7.61 (m, 2H), 7.56 (t, J=7.7 Hz, 1H), 7.52-7.43 (m, 2H), 7.43-7.33 (m, 2H), 6.96 (dt, J=7.5, 0.8 Hz, 1H), 5.26 (s, 2H), 4.99 (ddd, J=8.2, 4.9, 2.1 Hz, 1H), 3.34-3.21 (m, 2H), 2.98-2.66 (m, 4H), 2.10 (m, 1H), 2.00-1.86 (m, 1H), 1.82 (s, 3H), 1.76-1.52 (m, 2H), 1.53-1.39 (m, 1H).

UPLC-MS: Rt 3.144 m/z 591.4-592.4 $[M+H]^+$.

The following examples, from 11 to 14, were synthesized using the procedure described for the Example 10.

Example 11: (S)-quinuclidin-3-yl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ 10.92 (s, 1H), 8.84 (d, J=4.5 Hz, 1H), 8.20-7.81 (m, 4H), 7.76-7.28 (m, 8H), 6.96 (d, J=7.4 Hz, 1H), 5.26 (s, 2H), 5.13-4.78 (m, 1H), 3.38-3.18 (m, 2H), 22.84-2.66 (m, 4H), 2.06 (s, 1H), 1.88-1.80 (m, 1H), 1.82 (s, 3H), 1.73-1.29 (m, 3H).

UPLC-MS: Rt 3.045 m/z 591.4-592.4 $[M+H]^+$.

Example 12: quinuclidin-4-yl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ 10.81 (d, J=9.3 Hz, 1H), 8.86 (d, J=4.4 Hz, 1H), 8.17 (d, J=2.1 Hz, 1H), 8.04 (d, J=8.2 Hz, 1H), 7.90-7.63 (m, 4H), 7.64-7.30 (m, 6H), 6.99 (d, J=7.5 Hz, 1H), 5.26 (s, 2H), 1.84 (s, 3H), 1.44-1.12 (m, 12H).

UPLC-MS: Rt 6.744 m/z 591.5-592.5 $[M+H]^+$.

Example 13: 2-(azetidin-1-yl)ethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ 10.97 (s, 1H), 8.86 (d, J=4.4 Hz, 1H), 8.17 (s, 1H), 8.10-8.00 (m, 2H), 7.90 (dt, J=10.9, 2.3 Hz, 1H), 7.81-7.29 (m, 7H), 6.98 (d, J=7.5 Hz, 1H), 5.28 (s, 2H), 4.24 (t, J=5.4 Hz, 2H), 3.18 (t, J=6.9 Hz, 4H), 2.69 (t, J=5.4 Hz, 2H), 1.96 (p, J=6.9 Hz, 2H), 1.84 (s, 3H).

UPLC-MS: Rt 3.887 m/z 565.5-566.5 $[M+H]^+$.

Example 14: 2-(aziridin-1-yl)ethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ 10.98 (s, 1H), 8.97-8.59 (m, 1H), 8.24-7.80 (m, 4H), 7.82-7.28 (m, 8H), 6.99 (d, J=7.5 Hz, 1H), 5.29 (s, 2H), 4.41 (t, J=5.3 Hz, 2H), 1.84 (s, 3H), 1.72-1.44 (m, 2H), 1.41-1.02 (m, 2H).

UPLC-MS: Rt 3.439 m/z 551.4-552.4 $[M+H]^+$.

Example 15: 2-(methylamino)ethyl 3-fluoro-5-(2-(3-(6-methylpyridin-2-yl)-4-(quinolin-4-yl)-1H-pyrazol-1-yl)acetamido)benzoate To a solution of tert-butyl 2-(3-(2-(3-(6-methylpyridin-2-yl)-4-(quinolin-4-yl)-1H-pyrazol-1-yl)acetamido)-5-fluorobenzoyloxy)ethylmethylcarbamate (0.30 g, 0.469 mmol) in dioxane (3 mL) HCl (0.58 mL, 2.34 mmol. Solution 4 M in dioxane) was added and the reaction mixture was stirred at room temperature for 4 h. The solvent was concentrated under reduced pressure and the residue was dissolved in a mixture of EtOAc (15 mL) and $NaHCO_3$ (10 mL, aqueous saturated solution). The phases were separated and the organic layer was washed with sodium bicarbonate (10 mL, aqueous saturated solution), ammonium chloride (10 mL, aqueous saturated solution), dried over sodium sulfate and concentrated. The reaction product was purified by C18 chromatography with a Combiflash system (5→80% MeCN:$H_2O$+0.1 formic acid) to afford a white solid (0.043 g, 17%).

$^1$H NMR (300 MHz, DMSO-$d_6$) δ=11.10 (s, 1H), 8.86 (d, J=4.4 Hz, 1H), 8.30 (s, 1H), 8.17 (s, 1H), 8.12-7.97 (m, 2H), 7.92 (dt, J=11.0, 2.3 Hz, 1H), 7.80-7.29 (m, 6H), 6.98 (d, J=7.4 Hz, 1H), 5.28 (s, 2H), 4.39 (t, J=5.3 Hz, 2H), 2.99 (t, J=5.3 Hz, 2H), 2.43 (s, 3H), 1.84 (s, 3H).

UPLC-MS: Rt 3.010 m/z 539.4-540.4 $[M+H]^+$.

The following examples 16-21 were synthesized using the procedure described for the Example 15 from the corresponding ester derivative.

Example 16: 2-aminoethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=11.19 (s, 1H), 8.83 (d, J=4.5 Hz, 1H), 8.31 (s, 1H), 8.14 (br s, 2H), 8.02 (d, J=8.3 Hz, 1H), 7.91 (d, J=10.8 Hz, 1H), 7.78-7.24 (m, 8H), 6.96 (d, J=7.5 Hz, 1H), 5.27 (s, 2H), 4.34 (br s, 2H), 3.07 (br s, 2H), 1.82 (s, 3H).

UPLC-MS: Rt 2.880 m/z 525.3-526.3 $[M+H]^+$.

Example 17: 2-(ethylamino)ethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ 11.11 (s, 1H), 8.85 (d, J=4.5 Hz, 1H), 8.30 (br s, 1H), 8.17 (s, 1H), 8.11 (br s, 1H), 8.04 (d, J=8.2 Hz, 1H), 7.91-7.89 (m, 1H), 7.80-7.29 (m, 7H), 6.98 (d, J=7.5 Hz, 1H), 5.28 (s, 2H), 4.38 (t, J=5.5 Hz, 2H), 3.01 (br s, 2H), 2.84-2.64 (m, 2H), 1.84 (s, 3H), 1.08 (t, J=7.1 Hz, 3H).

UPLC-MS: Rt 3.016 m/z 553.3-554.3 $[M+H]^+$.

Example 18: 2-(isopropylamino)ethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=11.14 (s, 1H), 8.85 (d, J=4.4 Hz, 1H), 8.29 (s, 1H), 8.17 (s, 1H), 8.12 (br s, 1H), 8.04 (d, J=8.3 Hz, 1H), 7.91 (dt, J=11.1, 2.3 Hz, 1H), 7.78-7.33 (m, 7H), 6.98 (d, J=7.5 Hz, 1H), 5.29 (s, 2H), 4.38 (t, J=5.6 Hz, 2H), 3.03 (t, J=5.6 Hz, 2H), 3.01-2.93 (m, 1H), 1.84 (s, 3H), 1.08 (d, J=6.2 Hz, 6H).

UPLC-MS: Rt 3.113 m/z 567.4-568.4 $[M+H]^+$.

Example 19: 2-(piperazin-1-yl)ethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=11.13 (s, 1H), 8.85 (d, J=4.4 Hz, 1H), 8.35 (s, 1H), 8.17 (s, 1H), 8.12-7.30 (m, 10H), 6.98 (d, J=7.6 Hz, 1H), 5.29 (s, 2H), 4.40 (t, J=5.5 Hz, 2H), 2.84 (br s, 4H), 2.79-2.63 (m, 2H), 1.84 (s, 3H).

UPLC-MS: Rt 3.070 m/z 594.4-595.4 $[M+H]^+$.

Example 20: piperidin-4-ylmethyl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=10.38 (s, 1H), 7.90 (br s, 1H), 7.42 (s, 1H), 7.21 (s, 1H), 7.17-6.90 (m, 3H), 6.87-6.32 (m, 7H), 6.02 (d, J=7.6 Hz, 1H), 4.34 (s, 2H), 3.24 (d, J=3.8 Hz, 2H), 2.28 (d, J=12.2 Hz, 2H), 1.85 (t, J=12.6 Hz, 2H), 1.06 (m, 1H), 0.86 (br s, 5H), 0.55 (q, J=12.4 Hz, 2H).

UPLC-MS: Rt 3.068 m/z 579.4-580.4 $[M+H]^+$.

Example 21: piperidin-4-yl 3-fluoro-5-(2-(3-(6-methylpyridin-2-yl)-4-(quinolin-4-yl)-1H-pyrazol-1-yl)acetamido)benzoate $^1$H NMR (300 MHz, DMSO-$d_6$) δ=11.11 (s, 1H), 8.85 (dd, J=4.6, 1.8 Hz, 1H), 8.49-7.80 (m, 5H), 7.80-7.26 (m, 7H), 6.98 (d, J=7.5 Hz, 1H), 5.29 (s, 2H), 5.14 (br s, 1H), 3.17 (br s, 2H), 2.95 (s, 2H), 2.11-1.93 (m, 2H), 1.84 (m, J=1.8 Hz, 5H).

UPLC-MS: Rt 3.012 m/z 565.4-566.4 $[M+H]^+$.

Comparative example 1: Cyclopropylmethyl 3-fluoro-5-(2-(3-(6-methylpyridin-2-yl)-4-(quinolin-4-yl)-1H-pyrazol-1-yl)acetamido)benzoate This compound was prepared following the procedure described in Example 1

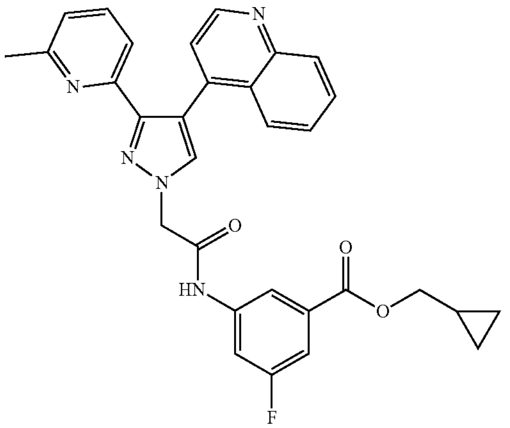 [SMILES: Cc1cccc(-c2nn(CC(=O)Nc3cc(F)cc(C(=O)OCC4CC4)c3)cc2-c2ccnc3ccccc23)n1]

$^1$H NMR (300 MHz, DMSO-$d_6$) δ 10.96 (s, 1H), 8.86 (m, 1H), 8.25-7.80 (m, 4H), 7.79-7.28 (m, 7H), 6.98 (d, J=7.6 Hz, 1H), 5.28 (s, 2H), 4.15 (d, J=8.0 Hz, 2H), 1.84 (br s, 3H), 1.24 (br s, 1H), 0.58 (d, J=7.5 Hz, 2H), 0.37 (br s, 2H).

UPLC-MS: Rt 4.16 m/z 536.5-537.5 $[M+H]^+$.

Comparative example 2: methyl 3-chloro-5-(2-(3-(6-methylpyridin-2-yl)-4-(quinolin-4-yl)-1H-pyrazol-1-yl)acetamido)benzoate

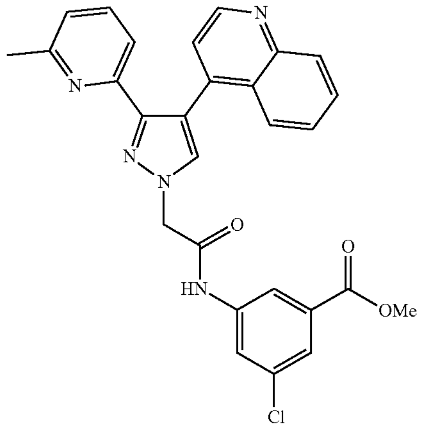 [SMILES: COC(=O)c1cc(Cl)cc(NC(=O)Cn2cc(-c3ccnc4ccccc34)c(-c3cccc(C)n3)n2)c1]

To a suspension of 4-(3-(6-methylpyridin-2-yl)-1H-pyrazol-4-yl)quinoline (0.3 g, 1.06 mmol) in DMF (8 mL) cooled with the aid of an external EtOH/ice bath, NaH (50 mg, 1.27 mmol. 60% dispersion in mineral oil) was added in one portion and the reaction mixture was stirred at low temperature for 20 min. A solution of methyl 3-(2-bromoacetamido)-5-chlorobenzoate (0.36 g, 1.17 mmol) in DMF (2 mL) was added dropwise and the mixture was stirred for 16 h, allowed to reach room temperature overnight. The reaction mixture was concentrated under reduced pressure and the crude residue was dissolved in $NH_4Cl$ (15 mL, aqueous saturated solution), extracted with dichloromethane (2×10 mL), dried over sodium sulfate and concentrated under reduced pressure. The residue was purified by flash chromatography on silice gel (0→3% $MeOH/CH_2Cl_2$) and by C18 chromatography with a Combiflash system (5→90% $H_2O$/MeOH) and the resulting solid was slurried with diethyl ether (2×3 mL) to afford a beige solid (0.257 g, 47%).

$^1$H NMR (300 MHz, DMSO-$d_6$) δ=10.93 (s, 1H), 8.86 (d, J=4.4 Hz, 1H), 8.44-7.84 (m, 4H), 7.81-7.23 (m, 7H), 6.98 (d, J=7.5 Hz, 1H), 5.28 (s, 2H), 3.88 (s, 3H), 1.83 (s, 3H).

HPLC-MS: Rt 19.792 m/z 512.1 $[M+H]^+$.

Comparative example 3: 2-hydroxyethyl 3-fluoro-5-(2-(3-(6-methylpyridin-2-yl)-4-(quinolin-4-yl)-1H-pyrazol-1-yl)acetamido)benzoate

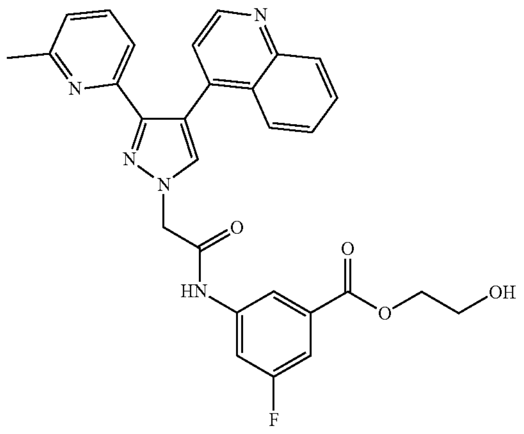 [SMILES: Cc1cccc(-c2nn(CC(=O)Nc3cc(F)cc(C(=O)OCCO)c3)cc2-c2ccnc3ccccc23)n1]

This compound was prepared following the procedure describe for example 1 but using $Et_3N$ instead of DIPEA.

$^1H$ NMR (300 MHz, DMSO-$d_6$) δ=10.99 (s, 1H), 8.85 (d, J=4.5 Hz, 1H), 8.25-7.83 (m, 4H), 7.78-7.34 (m, 7H), 6.98 (d, J=7.5 Hz, 1H), 5.28 (s, 2H), 4.98 (br s, 1H), 4.31 (t, J=4.9 Hz, 2H), 3.71 (br s, 2H), 1.84 (s, 3H).

UPLC-MS: Rt 3.135 m/z 526.4-527.4 [M+H]$^+$.

The invention claimed is:

1. A compound of formula (I):

(I)

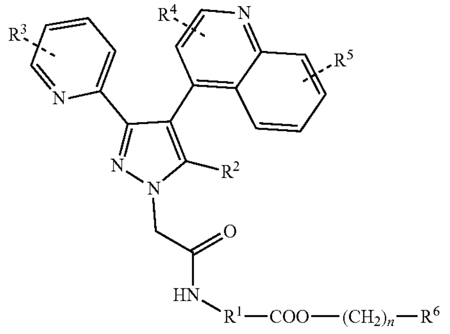

wherein:

$R^1$ represents a group selected from:

a) phenyl ring unsubstituted or substituted by 1 or 2 groups selected from halogen, linear or branched $C_1$-$C_3$ haloalkyl, linear or branched $C_1$-$C_3$ alkyl, linear or branched $C_1$-$C_3$ alkoxy, cyano and hydroxy, and b) 5- or 6-membered heteroaryl ring unsubstituted or substituted by 1 or 2 groups selected from halogen, linear or branched $C_1$-$C_3$ haloalkyl, linear or branched $C_1$-$C_3$ alkyl, linear or branched $C_1$-$C_3$ alkoxy, cyano and hydroxy;

$R^2$ represents a group selected from:

a) hydrogen, and b) linear or branched $C_1$-$C_3$ alkyl optionally substituted by 1, 2, or 3 halogen atoms;

$R^3$ represents a group selected from:

a) hydrogen, b) linear or branched $C_1$-$C_3$ alkyl optionally substituted by 1, 2, or 3 halogen atoms, and c) halogen atom, $R^4$ and $R^5$ independently represent a group selected from:

a) hydrogen, b) linear or branched $C_1$-$C_3$ alkyl optionally substituted by 1, 2, or 3 halogen atoms, and c) halogen;

n is an integer from 0 to 3;

$R^6$ represents a group selected from the group consisting of:

a) —N($R^7$)($R^8$), wherein $R^7$ and $R^8$ are independently selected from linear or branched $C_1$-$C_6$ alkyl or hydrogen, and b) saturated 4- to 10-membered, monocyclic or bicyclic, nitrogen-containing heterocyclyl optionally comprising another heteroatom selected from the group consisting of oxygen and nitrogen, said heterocyclyl being optionally substituted by $C_1$-$C_3$ alkyl;

or a pharmaceutically acceptable salt thereof.

2. The compound or a pharmaceutically acceptable salt thereof according to claim 1, wherein $R^2$, $R^4$, and $R^5$ are hydrogen.

3. The compound or a pharmaceutically acceptable salt thereof according to claim 1, wherein $R^3$ is methyl.

4. The compound or a pharmaceutically acceptable salt thereof according to claim 1, wherein $R^1$ is phenyl substituted by 1 or 2 halogen atoms.

5. The compound or a pharmaceutically acceptable salt thereof according to claim 1, wherein n is an integer from 1 to 2 and $R^6$ is —N($R^7$)($R^8$).

6. The compound or a pharmaceutically acceptable salt thereof according to claim 5, wherein $R^7$ and $R^8$ are independently a selected from linear $C_1$-$C_3$ alkyl or hydrogen.

7. The compound or a pharmaceutically acceptable salt thereof according to claim 1, wherein $R^6$ is a saturated 6-membered heterocyclic group containing 1 or 2 nitrogen atoms, optionally substituted by a methyl group.

8. The compound or a pharmaceutically acceptable salt thereof according to claim 7, wherein $R^6$ is selected from piperazinyl and piperidinyl.

9. The compound or a pharmaceutically acceptable salt thereof according to claim 1, wherein $R^2$, $R^4$, and $R^5$ are hydrogen atom, $R^3$ is linear $C_1$-$C_3$ alkyl, $R^1$ is phenyl ng substituted by 1 or 2 halogen atoms, n is an integer from 0 to 2, and $R^6$ is selected from the group consisting of:

a) —N($R^7$)($R^8$), wherein $R^7$ and $R^8$ are independently selected from linear $C_1$-$C_3$alkyl and hydrogen, b) a saturated 6-membered heterocyclic group containing 1 or 2 nitrogen atoms, optionally substituted by a methyl group, and c) 1-aza-bicyclo[2.2.2]octanyl.

10. The compound or a pharmaceutically acceptable salt thereof according to claim 1, which is selected from:

2-(dimethylamino)ethyl 3-fluoro-5-(2-(3-(6-methylpyridin-2-yl)-4-(quinolin-4-yl)-1H-pyrazol-1-yl)acetamido)benzoate;

2-(dimethylamino)ethyl 5-(2-(3-(6-methylpyridin-2-yl)-4-(quinolin-4-yl)-1H-pyrazol-1-yl)acetamido)nicotinate;

2-(dimethylamino)ethyl 6-(2-(3-(6-methylpyridin-2-yl)-4-(quinolin-4-yl)-1H-pyrazol-1-yl)acetamido)nicotinate;

2-morpholinoethyl 3-fluoro-5-(2-(3-(6-methylpyridin-2-yl)-4-(quinolin-4-yl)-1H-pyrazol-1-yl)acetamido)benzoate;

2-(dimethylamino)ethyl 5-(2-(3-(6-methylpyridin-2-yl)-4-(quinolin-4-yl)-1H-pyrazol-1-yl)acetamido)picolinate;

2-(4-methylpiperazin-1-yl)ethyl 3-fluoro-5-(2-(3-(6-methylpyridin-2-yl)-4-(quinolin-4-yl)-1H-pyrazol-1-yl)acetamido)benzoate;

2-(diethylamino)ethyl 3-fluoro-5-(2-(3-(6-methylpyridin-2-yl)-4-(quinolin-4-yl)-1H-pyrazol-1-yl)acetamido) benzoate;

1-methylpiperidin-4-yl 3-fluoro-5-(2-(3-(6-methylpyridin-2-yl)-4-(quinolin-4-yl)-1H-pyrazol-1-yl)acetamido)benzoate;

(1-methylpiperidin-4-yl)methyl 3-fluoro-5-(2-(3-(6-methylpyridin-2-yl)-4-(quinolin-4-yl)-1H-pyrazol-1-yl)acetamido)benzoate;

(R)-quinuclidin-3-yl 3-fluoro-5-(2-(3-(6-methylpyridin-2-yl)-4-(quinolin-4-yl)-1H-pyrazol-1-yl)acetamido) benzoate;

(S)-quinuclidin-3-yl 3-fluoro-5-(2-(3-(6-methylpyridin-2-yl)-4-(quinolin-4-yl)-1H-pyrazol-1-yl)acetamido) benzoate;

quinuclidin-4-yl 3-fluoro-5-(2-(3-(6-methylpyridin-2-yl)-4-(quinolin-4-yl)-1H-pyrazol-1-yl)acetamido)benzoate;

2-(azetidin-1-yl)ethyl 3-fluoro-5-(2-(3-(6-methylpyridin-2-yl)-4-(quinolin-4-yl)-1H-pyrazol-1-yl)acetamido) benzoate;

2-(aziridin-1-yl)ethyl 3-fluoro-5-(2-(3-(6-methylpyridin-2-yl)-4-(quinolin-4-yl)-1H-pyrazol-1-yl)acetamido) benzoate;

2-(methylamino)ethyl 3-fluoro-5-(2-(3-(6-methylpyridin-2-yl)-4-(quinolin-4-yl)-1H-pyrazol-1-yl)acetamido) benzoate;

2-aminoethyl 3-fluoro-5-(2-(3-(6-methylpyridin-2-yl)-4-(quinolin-4-yl)-1H-pyrazol-1-yl)acetamido)benzoate;

2-(ethylamino)ethyl 3-fluoro-5-(2-(3-(6-methylpyridin-2-yl)-4-(quinolin-4-yl)-1H-pyrazol-1-yl)acetamido)benzoate;

2-(isopropylamino)ethyl 3-fluoro-5-(2-(3-(6-methylpyridin-2-yl)-4-(quinolin-4-yl)-1H-pyrazol-1-yl)acetamido)benzoate;

2-(piperazin-1-yl)ethyl 3-fluoro-5-(2-(3-(6-methylpyridin-2-yl)-4-(quinolin-4-yl)-1H-pyrazol-1-yl)acetamido)benzoate;

piperidin-4-ylmethyl 3-fluoro-5-(2-(3-(6-methylpyridin-2-yl)-4-(quinolin-4-yl)-1H-pyrazol-1-yl)acetamido) benzoate;

piperidin-4-yl 3-fluoro-5-(2-(3-(6-methylpyridin-2-yl)-4-(quinolin-4-yl)-1H-pyrazol-1-yl)acetamido)benzoate;

or a pharmaceutically acceptable salt of any one thereof.

11. The compound or a pharmaceutically acceptable salt thereof according to claim 1, which is 2-(dimethylamino) ethyl 3-fluoro-5-(2-(3-(6-methylpyridin-2-yl)-4-(quinolin-4-yl)-1H-pyrazol-1-yl)acetamido)benzoate.

12. The compound or a pharmaceutically acceptable salt thereof according to claim 1, which is the pharmaceutically acceptable salt of 2-(dimethylamino)ethyl 3-fluoro-5-(2-(3-(6-methylpyridin-2-yl)-4-(quinolin-4-yl)-1H-pyrazol-1-yl) acetamido)benzoate.

13. The compound or a pharmaceutically acceptable salt thereof according to claim 1, which is (1-methylpiperidin-4-yl)methyl 3-fluoro-5-(2-(3-(6-methylpyridin-2-yl)-4-(quinolin-4-yl)-1H-pyrazol-1-yl)acetamido)benzoate.

14. The compound or a pharmaceutically acceptable salt thereof according to claim 1, which is the pharmaceutically acceptable salt of (1-methylpiperidin-4-yl)methyl 3-fluoro-5-(2-(3-(6-methylpyridin-2-yl)-4-(quinolin-4-yl)-1H-pyrazol-1-yl)acetamido)benzoate.

15. The compound or a pharmaceutically acceptable salt thereof according to claim 1, which is 2-(piperazin-1-yl) ethyl 3-fluoro-5-(2-(3-(6-methylpyridin-2-yl)-4-(quinolin-4-yl)-1H-pyrazol-1-yl)acetamido)benzoate.

16. The compound or a pharmaceutically acceptable salt thereof according to claim 1, which is the pharmaceutically acceptable salt of 2-(piperazin-1-yl)ethyl 3-fluoro-5-(2-(3-(6-methylpyridin-2-yl)-4-(quinolin-4-yl)-1H-pyrazol-1-yl) acetamido)benzoate.

17. A pharmaceutical composition comprising the compound or pharmaceutically acceptable salt thereof according to claim 1 and a pharmaceutically acceptable diluent or carrier.

18. The pharmaceutical composition according to claim 17, further comprising a therapeutically effective amount of a therapeutic agent useful for the treatment of a disease or a pathological condition selected from pulmonary fibrosis, asthma, chronic obstructive pulmonary disease, idiopathic pulmonary fibrosis, lung cancer, or a fibrotic eye disease.

19. The pharmaceutical composition according to claim 18, wherein the disease or pathological condition is idiopathic pulmonary fibrosis.

20. A combination product comprising the compound or pharmaceutically acceptable salt thereof according to claim 1 and at least one therapeutic agent useful for the treatment of a disease or a pathological condition wherein the disease or pathological condition is selected from pulmonary fibrosis, asthma, chronic obstructive pulmonary disease, idiopathic pulmonary fibrosis, lung cancer or a fibrotic eye disease.

21. The combination product according to claim 20, wherein the disease or pathological condition is idiopathic pulmonary fibrosis.

22. A method for the treatment of a disease or a pathological condition selected from pulmonary fibrosis, asthma, chronic obstructive pulmonary disease, idiopathic pulmonary fibrosis, lung cancer, or a fibrotic eye disease, comprising: administering to a patient in need thereof of a therapeutically effective amount of the compound or pharmaceutically acceptable salt thereof according to claim 1.

23. The method according to claim 22, wherein the disease or pathological condition is idiopathic pulmonary fibrosis.

24. The method according to claim 23, wherein the compound or pharmaceutically acceptable salt of formula (I) is 2-(dimethylamino)ethyl 3-fluoro-5-(2-(3-(6-methylpyridin-2-yl)-4-(quinolin-4-yl)-1H-pyrazol-1-yl)acetamido) benzoate.

25. The method according to claim 23, wherein the compound or pharmaceutically acceptable salt of formula (I) is the pharmaceutically acceptable salt of 2-(dimethylamino) ethyl 3-fluoro-5-(2-(3-(6-methylpyridin-2-yl)-4-(quinolin-4-yl)-1H-pyrazol-1-yl)acetamido)benzoate.

26. The method according to claim 23, wherein the compound or pharmaceutically acceptable salt of formula (I) is (1-methylpiperidin-4-yl)methyl 3-fluoro-5-(2-(3-(6-methylpyridin-2-yl)-4-(quinolin-4-yl)-1H-pyrazol-1-yl)acetamido)benzoate.

27. The method according to claim 23, wherein the compound or pharmaceutically acceptable salt of formula (I) is the pharmaceutically acceptable salt of (1-methylpiperidin-4-yl)methyl 3-fluoro-5-(2-(3-(6-methylpyridin-2-yl)-4-(quinolin-4-yl)-1H-pyrazol-1-yl)acetamido)benzoate.

28. The method according to claim 23, wherein the compound or pharmaceutically acceptable salt of formula (I) is 2-(piperazin-1-yl)ethyl 3-fluoro-5-(2-(3-(6-methylpyridin-2-yl)-4-(quinolin-4-yl)-1H-pyrazol-1-yl)acetamido) benzoate.

29. The method according to claim 23, wherein the compound or pharmaceutically acceptable salt of formula (I) is the pharmaceutically acceptable salt of 2-(piperazin-1-yl) ethyl 3-fluoro-5-(2-(3-(6-methylpyridin-2-yl)-4-(quinolin-4-yl)-1H-pyrazol-1-yl)acetamido)benzoate.

30. A method for the preparation of the compound according to claim 1 or salt thereof comprising: reacting a compound of formula (II):

(II)

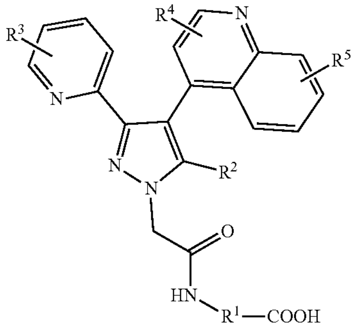

or a salt thereof, with a compound of formula (III):

$$OH—(CH_2)_n—R^6 \quad (III)$$

or a salt thereof, wherein:

$R^1$ represents a group selected from:

a) phenyl ring unsubstituted or substituted by 1 or 2 groups selected from halogen-atm, linear or branched $C_1$-$C_3$ haloalkyl, linear or branched $C_1$-$C_3$ alkyl, linear or branched $C_1$-$C_3$ alkoxy, cyano and hydroxy, b) 5- or 6-membered heteroaryl ring unsubstituted or substituted by 1 or 2 groups selected from halogen, linear or branched $C_1$-$C_3$ haloalkyl, linear or branched $C_1$-$C_3$ alkyl, linear or branched $C_1$-$C_3$ alkoxy, cyano and hydroxy, $R^2$ represents a group selected from:

a) hydrogen, and b) linear or branched $C_1$-$C_3$ alkyl optionally substituted by 1, 2, or 3 halogen atoms, $R^3$ represents a group selected from:

a) hydrogen, b) linear or branched $C_1$-$C_3$ alkyl optionally substituted by 1, 2, or 3 halogen atoms, and c) halogen, $R^4$ and $R^5$ independently represent a group selected from:

a) hydrogen, b) linear or branched $C_1$-$C_3$ alkyl optionally substituted by 1, 2, or 3 halogen atoms, and c) halogen, n is an integer from 0 to 3, $R^6$ represents a group selected from the group consisting of:

a) —$N(R^7)(R^8)$, wherein $R^7$ and $R^8$ are independently selected from linear or branched $C_1$-$C_6$ alkyl group or hydrogen, and b) saturated 4- to 10-membered, monocyclic or bicyclic, nitrogen-containing heterocyclyl optionally comprising another heteroatom selected from the group consisting of oxygen and nitrogen, said heterocyclyl being optionally substituted by $C_1$-$C_3$ alkyl.

* * * * *